US009513177B2

(12) United States Patent
Shalom et al.

(10) Patent No.: US 9,513,177 B2
(45) Date of Patent: Dec. 6, 2016

(54) SYSTEM AND METHOD FOR RAPID DATA COLLECTION FROM PRESSURE SENSORS IN A PRESSURE SENSING SYSTEM

(75) Inventors: Amir Ben Shalom, Modiin (IL); Itai Raab, Hod Hasharon (IL); Tal (Nathan) Remez, Tel Aviv (IL); Boaz Ben David, Tel-Aviv (IL); Dan Weiss, Ramat Hasharon (IL); Ruth Poliakine, Tel Aviv (IL); Lior Greenstein, Tel-Aviv (IL); Yonatan Assuline, Kfar Billu A' (IL); Gusti Averbuch, Modiin (IL); Tsahi Asher, Modiin (IL)

(73) Assignee: Enhanced Surface Dynamics, Inc., Wellesley, MA (US)

( * ) Notice: Subject to any disclaimer, the term of this patent is extended or adjusted under 35 U.S.C. 154(b) by 1090 days.

(21) Appl. No.: 13/580,058

(22) PCT Filed: Mar. 10, 2011

(86) PCT No.: PCT/IB2011/051016
§ 371 (c)(1),
(2), (4) Date: Nov. 13, 2012

(87) PCT Pub. No.: WO2011/111021
PCT Pub. Date: Sep. 15, 2011

(65) Prior Publication Data
US 2013/0191057 A1    Jul. 25, 2013

Related U.S. Application Data

(60) Provisional application No. 61/313,249, filed on Mar. 12, 2010, provisional application No. 61/325,988, filed on Apr. 20, 2010, provisional application No. 61/328,726, filed on Apr. 28, 2010, provisional application No. 61/351,554, filed on Jun. 4, 2010.

(51) Int. Cl.
*G01R 19/00* (2006.01)
*G01L 1/14* (2006.01)
(Continued)

(52) U.S. Cl.
CPC ............... *G01L 1/144* (2013.01); *A61B 5/103* (2013.01); *A61B 5/445* (2013.01); *A61B 5/447* (2013.01);
(Continued)

(58) Field of Classification Search
USPC ......................................................... 702/64
See application file for complete search history.

(56) References Cited

U.S. PATENT DOCUMENTS 4,503,286 A    3/1985    Kubo et al.
4,526,043 A    7/1985    Boie et al.
(Continued)

FOREIGN PATENT DOCUMENTS

DE    3227550        1/1983
EP    0264047 A2    4/1988
(Continued)

OTHER PUBLICATIONS

International Search Report and Written Opinion for PCT/IB13/52878 dated Oct. 29, 2013.
(Continued)

*Primary Examiner* — Paul D Lee
(74) *Attorney, Agent, or Firm* — Brooks Kushman P.C.

(57) ABSTRACT

A system and method for the management of data collection from a pressure sensing apparatus. The system allows rapid measurement of pressure exerted upon a surface and may be useful in preventing bed sore development in a bed bound subject.

20 Claims, 16 Drawing Sheets

(51) Int. Cl.
  *A61B 5/103* (2006.01)
  *A61B 5/00* (2006.01)
  *G06F 15/00* (2006.01)
  *G06F 17/50* (2006.01)

(52) U.S. Cl.
  CPC ............. *A61B 5/6892* (2013.01); *G01L 1/146* (2013.01); *G06F 15/00* (2013.01); *G06F 17/5009* (2013.01); *A61B 2562/0247* (2013.01); *A61B 2562/046* (2013.01)

(56) References Cited

U.S. PATENT DOCUMENTS

| | | |
|---|---|---|
| 4,554,930 A | 11/1985 | Kress |
| 4,758,815 A | 7/1988 | Lovell |
| 4,795,998 A | 1/1989 | Dunbar et al. |
| 4,827,763 A | 5/1989 | Bourland et al. |
| 4,929,803 A | 5/1990 | Yoshida et al. |
| 5,010,772 A | 4/1991 | Bourland et al. |
| 5,030,508 A | 7/1991 | Kuhn et al. |
| 5,033,291 A | 7/1991 | Podoloff et al. |
| 5,086,652 A | 2/1992 | Kropp |
| 5,102,727 A | 4/1992 | Pittman et al. |
| 5,131,259 A | 7/1992 | Kropp |
| 5,162,135 A | 11/1992 | Gregory et al. |
| 5,276,432 A | 1/1994 | Travis |
| 5,505,072 A | 4/1996 | Oreper |
| 5,571,973 A | 11/1996 | Taylot |
| 5,642,096 A | 6/1997 | Leyerer et al. |
| 5,720,892 A | 2/1998 | DeAngelis et al. |
| 5,756,904 A | 5/1998 | Oreper et al. |
| 5,808,552 A | 9/1998 | Wiley et al. |
| 5,905,209 A | 5/1999 | Oreper |
| 5,942,733 A | 8/1999 | Allen et al. |
| 5,970,789 A | 10/1999 | Meyer et al. |
| 5,993,400 A | 11/1999 | Rincoe et al. |
| 6,014,346 A | 1/2000 | Malone |
| 6,032,542 A | 3/2000 | Warnick et al. |
| 6,067,019 A | 5/2000 | Scott |
| 6,155,120 A | 12/2000 | Taylor |
| 6,216,545 B1 | 4/2001 | Taylor |
| 6,216,546 B1 | 4/2001 | Bahr |
| 6,225,814 B1 | 5/2001 | Oreper et al. |
| 6,244,272 B1 | 6/2001 | Montant et al. |
| 6,287,253 B1 | 9/2001 | Ortega et al. |
| 6,367,106 B1 | 4/2002 | Gronsman |
| 6,386,051 B1 | 5/2002 | Yoshimi et al. |
| 6,417,777 B2 | 7/2002 | Fitzgerald et al. |
| 6,432,737 B1 | 8/2002 | Webster |
| 6,438,776 B2 | 8/2002 | Ferrand et al. |
| 6,441,742 B1 | 8/2002 | Lovely et al. |
| 6,543,299 B2 | 4/2003 | Taylor |
| 6,546,813 B2 | 4/2003 | Hubbard, Jr. |
| 6,721,980 B1 | 4/2004 | Price et al. |
| 6,897,781 B2 | 5/2005 | Cooper et al. |
| 6,945,115 B1 | 9/2005 | Wang |
| 6,964,205 B2 | 11/2005 | Papakostas et al. |
| 6,987,232 B2 | 1/2006 | Smith et al. |
| 6,993,954 B1 | 2/2006 | George et al. |
| 7,030,764 B2 | 4/2006 | Smith et al. |
| 7,090,647 B2 | 8/2006 | Mimura et al. |
| 7,119,696 B2 | 10/2006 | Borugian |
| 7,201,063 B2 | 4/2007 | Taylor |
| 7,258,026 B2 | 8/2007 | Papakostas et al. |
| 7,304,580 B2 | 12/2007 | Sullivan et al. |
| 7,319,386 B2 | 1/2008 | Collins, Jr. et al. |
| 7,330,127 B2 | 2/2008 | Price et al. |
| 7,377,133 B2 | 5/2008 | Sandbach et al. |
| 7,378,975 B1 | 5/2008 | Smith et al. |
| 7,464,605 B2 | 12/2008 | Douglas et al. |
| 7,480,951 B2 | 1/2009 | Weismiller et al. |
| 7,531,203 B2 | 5/2009 | Tao et al. |
| 7,557,718 B2 | 7/2009 | Petrosenko et al. |
| 7,559,106 B1 | 7/2009 | Crousore et al. |
| 7,568,246 B2 | 8/2009 | Weismiller et al. |
| 7,591,165 B2 | 9/2009 | Loomis et al. |
| 7,629,890 B2 | 12/2009 | Sullivan et al. |
| 7,652,581 B2 | 1/2010 | Gentry et al. |
| 7,656,299 B2 | 2/2010 | Gentry et al. |
| 7,714,238 B2 | 5/2010 | Skinner et al. |
| 7,746,218 B2 | 6/2010 | Collins, Jr. et al. |
| 7,752,926 B2 | 7/2010 | Caminade et al. |
| 7,825,814 B2 | 11/2010 | Lokhorst et al. |
| 7,849,545 B2 | 12/2010 | Flocard et al. |
| 7,852,208 B2 | 12/2010 | Collins et al. |
| 7,868,740 B2 | 1/2011 | McNeely et al. |
| 8,011,041 B2 | 9/2011 | Hann |
| 8,117,701 B2 | 2/2012 | Bobey et al. |
| 8,121,800 B2 | 2/2012 | Altman et al. |
| 8,272,276 B2 | 9/2012 | Gorjanc et al. |
| 8,413,271 B2 | 4/2013 | Blanchard et al. |
| 2002/0121146 A1 | 9/2002 | Manaresi et al. |
| 2003/0105389 A1 | 6/2003 | Noonan et al. |
| 2004/0046668 A1 | 3/2004 | Smith et al. |
| 2004/0059199 A1 | 3/2004 | Thomas et al. |
| 2005/0076715 A1 | 4/2005 | Kuklis et al. |
| 2005/0165284 A1 | 7/2005 | Gefen |
| 2006/0028350 A1 | 2/2006 | Bhai |
| 2006/0065060 A1 | 3/2006 | Ito et al. |
| 2006/0152378 A1 | 7/2006 | Lokhorst et al. |
| 2006/0213286 A1 | 9/2006 | De Arenaza |
| 2006/0293613 A1 | 12/2006 | Fatehi et al. |
| 2007/0008156 A1 | 1/2007 | Ueda et al. |
| 2007/0234825 A1 | 10/2007 | Loomis et al. |
| 2007/0235231 A1 | 10/2007 | Loomis et al. |
| 2008/0009686 A1 | 1/2008 | Hendrich |
| 2008/0060138 A1 | 3/2008 | Price et al. |
| 2008/0078030 A1 | 4/2008 | Lee et al. |
| 2008/0169931 A1 | 7/2008 | Gentry et al. |
| 2008/0183048 A1 | 7/2008 | Zhang |
| 2008/0202251 A1 | 8/2008 | Serban |
| 2008/0275326 A1 | 11/2008 | Kasielke et al. |
| 2009/0044334 A1 | 2/2009 | Parsell et al. |
| 2009/0069727 A1 | 3/2009 | Neustaedter et al. |
| 2009/0070939 A1 | 3/2009 | Hann |
| 2009/0099480 A1 | 4/2009 | Salgo et al. |
| 2009/0119843 A1 | 5/2009 | Rodgers et al. |
| 2009/0129031 A1 | 5/2009 | Someya et al. |
| 2009/0129556 A1 | 5/2009 | Ahn |
| 2010/0052917 A1 | 3/2010 | Sullivan et al. |
| 2010/0162832 A1 | 7/2010 | Brauers |
| 2010/0268122 A1 | 10/2010 | Drennan et al. |
| 2010/0298742 A1 | 11/2010 | Perlman et al. |
| 2010/0308846 A1 | 12/2010 | Camus |
| 2011/0001622 A1 | 1/2011 | Gentry et al. |
| 2011/0030141 A1 | 2/2011 | Soderberg et al. |
| 2011/0035057 A1 | 2/2011 | Receveur et al. |
| 2011/0046498 A1 | 2/2011 | Klap et al. |
| 2011/0068932 A1 | 3/2011 | Flocard et al. |
| 2011/0156915 A1 | 6/2011 | Brauers et al. |
| 2011/0234408 A1 | 9/2011 | Dixon et al. |
| 2011/0263950 A1 | 10/2011 | Larson et al. |
| 2011/0302719 A1 | 12/2011 | Schwirian et al. |
| 2011/0308019 A1 | 12/2011 | Terawaki et al. |
| 2012/0184862 A1 | 7/2012 | Foo et al. |
| 2012/0253142 A1 | 10/2012 | Meger et al. |
| 2012/0277637 A1 | 11/2012 | Vahdatpour et al. |
| 2012/0323501 A1 | 12/2012 | Sarrafzadeh et al. |
| 2013/0091961 A1 | 4/2013 | Taylor |

FOREIGN PATENT DOCUMENTS

| | | |
|---|---|---|
| EP | 0480471 A2 | 4/1992 |
| EP | 1211633 | 6/2004 |
| EP | 2392304 A1 | 12/2011 |
| JP | H02-078925 | 3/1990 |
| JP | 02232050 A | 9/1990 |
| JP | 6201502 A2 | 7/1994 |
| JP | H06281516 | 10/1994 |
| JP | H07-65943 | 7/1995 |
| JP | 10024073 A | 1/1998 |
| JP | 20020126007 A | 5/2002 |
| JP | 2004-245822 | 9/2004 |
| JP | 2004-363759 | 12/2004 |

(56) References Cited

FOREIGN PATENT DOCUMENTS

| | | |
|---|---|---|
| JP | 2005237684 A | 9/2005 |
| JP | 2006-094903 | 4/2006 |
| JP | 2008027030 A | 2/2008 |
| JP | 2008-216016 | 9/2008 |
| JP | 2010012335 A | 1/2010 |
| JP | 2010-043881 | 2/2010 |
| WO | 2007106040 A1 | 9/2007 |
| WO | 2007121586 | 11/2007 |
| WO | 2009048617 | 4/2009 |
| WO | 2009065109 | 5/2009 |
| WO | 2009138976 A2 | 11/2009 |
| WO | 2010092517 A1 | 8/2010 |
| WO | 2010102309 A1 | 9/2010 |
| WO | 2010119441 | 10/2010 |
| WO | 2010119441 A2 | 10/2010 |
| WO | 2011091617 | 8/2011 |
| WO | 2011111021 | 9/2011 |
| WO | 2011113070 A1 | 9/2011 |
| WO | 2012056405 | 5/2012 |
| WO | 2012114298 | 8/2012 |
| WO | 2013008187 | 1/2013 |
| WO | 2013021376 A1 | 2/2013 |
| WO | 2013105028 | 7/2013 |
| WO | 2013156907 | 10/2013 |
| WO | 2014/024094 | 2/2014 |
| WO | 2014024094 A2 | 2/2014 |
| WO | 2014064596 A2 | 5/2014 |

OTHER PUBLICATIONS

International Search Report and Written Opinion for PCT/IB2013/056287 dated Feb. 10, 2014.
International Search Report and Written Opinion for PCT/IL2010/000294 dated Oct. 26, 2010.
International Search Report and Written Opinion for PCT/IB2011/051016 dated Oct. 9, 2012.
International Search Report and Written Opinion for PCT/IB2011/054773 dated Jun. 15, 2012.
International Search Report and Written Opinion for PCT/IB12/50829 dated Sep. 17, 2012.
International Search Report and Written Opinion for PCT/IB2012/053538 dated Dec. 17, 2012.
European Patent Office, Office Action for the corresponding European Patent Application No. 10 720 826.6 dated Apr. 16, 2014.
International Searching Authority, The International Search Report and the Written Opinion for the corresponding International Application No. PCT/IB13/59499 mailed May 20, 2014.
Muhammad Ahsen Khan, Dyeing of Wood and Silk Fibres with a Conductive Polyelectrolyte and Comparing Their Conductance, Report No. 2011.7.10, Masters in Textile Technology, University of Boras 2011.
Mehdi Nouri, et al. Iranian Polymer Journal, Archive of SID, Conductivity of Textile Fibers Treated with Aniline, vol. 9, No. 1, Feb. 8, 2000.
Office Action for U.S. Appl. No. 13/881,169 dated May 7, 2015.
International Search Report and Written Opinion for PCT/IB2013/050173 dated Jul. 1, 2013.
International Search Report for PCT/IB2015/051822 dated Jul. 6, 2015, 4 pages.
International Written Opinion for PCT/IB2015/051822 dated Jul. 6, 2015, 6 pages.
Final Office Action for U.S. Appl. No. 13/881,169 dated Sep. 24, 2015.
European Patent Office, Extended Search Report for the corresponding European Patent Application No. 12810788.5 mailed Feb. 2, 2015.

SYSTEM AND METHOD FOR RAPID DATA COLLECTION FROM PRESSURE SENSORS IN A PRESSURE SENSING SYSTEM

CROSS-REFERENCE TO RELATED APPLICATION

This application is the U.S. national phase of PCT Appln. No. PCT/IB2011/051016 filed Mar. 10, 2011 which claims the benefit of U.S. provisional application Ser. No. 61/313,249 filed Mar. 12, 2010, Ser. No. 61/325,988 filed Apr. 20, 2010, Ser. No. 61/328,726 filed Apr. 28, 2010 and Ser. No. 61/351,554 filed Jun. 4, 2010, the disclosures of which are incorporated in their entirety by reference herein.

TECHNICAL FIELD

The system and method described herein relate to quick and effective data collection from pressure sensors in a pressure sensing system.

BACKGROUND

Pressure wounds such as decubitus ulcers, which are commonly known as pressure ulcers or bedsores, are lesions developed when a localized area of soft tissue is compressed between a bony prominence and an external surface for a prolonged period of time. Pressure ulcers may appear in various parts of the body, and their development is affected by a combination of factors such as unrelieved pressure, friction, shearing forces, humidity and temperature.

Currently, about 10%-15% of hospitalized patients are estimated to have bedsores at any one time (Source: Medicare website 2009). However, it is not only hospitalized patients who suffer from pressure wounds: for example, people confined to wheelchairs are prone to suffer from pressure wounds, especially in their pelvis, lower back and ankles. Although easily prevented and completely treatable if found early, bedsores are painful, and treatment is both difficult and expensive. In many cases bedsores can prove fatal—even under the auspices of medical care.

The most effective way of dealing with pressure wounds is to prevent them. Existing preventive solutions are either passive (e.g. various types of cushioning) or active.

Active preventative solutions include manual or automatic redistribution of pressure. The most common active preventive approach is to maintain a strict routine of relieving pressure from sensitive body areas of a patient every two to three hours or so. Such a routine may be maintained for patients under constant medical care however, it is a difficult, labor intensive and costly task which does not meet the needs of individuals not requiring ongoing supervision of a caretaker.

Another active preventative approach to bedsores includes using a dynamic mattress that alternately inflates and deflates air cells so as to redistribute supportive pressure upon the patient. However, such mattresses typically redistribute pressure in a patient independent manner, including from less sensitive regions thereby needlessly or even actually detrimentally creating higher pressure in sensitive areas.

The applicants' copending international patent application WO 2010/119441, which is incorporated herein by reference, discloses a pressure sensing system for use in preventing decubitus ulcers, or bedsores, which comprises a sensing-mat including a plurality of sensors configured to detect pressure applied to body parts of a subject resting on a surface such as a bed or a chair. Information received from the sensors is analyzed by the system, which further issues alerts according to sensor readings.

Obtaining accurate values from measurement sensors may be difficult. Moreover, measurements may take a significant amount of time, for example when it takes time for a sensor to stabilize into a resting position in response to pressure changes. Time elapsed from the moment a pressure change occurs until a stable sensor reading is reached may be critical in real-time scenarios. Belated sensor readings may prevent systems from issuing relevant alerts in a timely manner.

Although this problem may be circumvented using costly materials or technologies that are quick to respond to changes, such materials are expensive and often excessively susceptible to amortization. Thus integrating complex technologies may both increase the cost and reduce the durability of sensor-based systems.

It will be appreciated that there is therefore a need for a cost-effective, reliable method for obtaining accurate reading values from sensors in a timely manner. The systems and methods disclosed hereinbelow address this need.

SUMMARY

Addressing the need for reliable and timely recordation of measured parameters, systems and methods are disclosed herein for the management of data collection from a pressure sensing apparatus. The system allows rapid measurement of pressure exerted upon a surface and may be useful in preventing bed sore development in a bed bound subject.

In one embodiment, a method is disclosed for measuring capacitances of n capacitors in a pressure sensing system. The pressure sensing system comprises: a plurality of linear conductor columns and a plurality of linear conductor rows, wherein the columns are not parallel to the rows, and an array of capacitors each formed at the intersection of a column and a row, and wherein the columns and rows are respectively disposed on opposite sides of a sheet of a compressible dielectric. Accordingly, the method comprises: applying an alternating known voltage to n circuits of the n capacitors, each of the n circuits comprising a different capacitor of the n capacitors being connected in series to the other n−1 capacitors, the n−1 capacitors being interconnected in parallel; measuring the alternating current of each of the n circuits; deriving total capacitance of each circuit from the known voltage and measured current; applying an alternating known voltage to an n+1 circuit comprising the n capacitors interconnected in parallel; measuring the alternating current of the n+1 circuit; deriving total capacitance of the n+1 circuit; and deriving from the measured and known values the capacitance of each of the n capacitors.

Optionally, the step of applying an alternating known voltage to n circuits comprises: applying an alternating known voltage between one row and a plurality of columns. Where appropriate, the step of measuring the alternating current of each of the n circuits may comprise: connecting a current sensor to one of the plurality of columns; and repeating the connecting for all of the plurality of columns. Optionally, the plurality of columns comprises all the linear conductor columns of the pressure sensing system.

In another embodiment, a method is disclosed for predicting a terminal-value of a parameter in a pressure sensing system, the method comprising the following steps: providing a mathematical model for the behavior of the parameter over time, the model comprising a formula expressing a relationship between the parameter and at least one variable; monitoring the parameter; acquiring a plurality of measured values for the parameter over time; calculating a best-fit set of values for the at least one variable based upon the plurality of measured values for the parameter; and using the set of values and the formula to determine a predicted terminal-value of the parameter for use in determining a pressure exerted upon the pressure sensing system.

Optionally, the method further includes providing initial values for the variables; acquiring a first monitored value for the parameter; adjusting the values of the variables to best-fit the first monitored value for the parameter; calculating a first predicted terminal-value of the parameter; acquiring a next value for the parameter; and adjusting the values of the variables to best-fit accrued monitored values of the parameter. Variously, the best-fit set of values are calculated using a method of least squares. Possibly, the plurality of measured values has one member.

Where appropriate, the mathematical model comprises an exponential relationship. Optionally, the exponential relationship has the form $$P=(P_F-P_0)(1-e^{-(t-t0)/\tau})+P_0,$$

wherein $P_F$ is the terminal-value of the parameter and $P_0$ is the initial value of the parameter.

Accordingly, a method is disclosed for measuring pressure acting upon a surface comprising the steps of: step (a)—providing at least one pressure sensor; step (b)—obtaining a formula expressing an exponential relationship between a measured pressure and a time-constant modeled after the behavior of the pressure sensor over time; step (c)—acquiring a plurality of pressure values over a time period; step (d)—calculating a best-fit value for the time-constant based upon the plurality of pressure values; and step (e)—using the time-constant value in the formula to determine a predicted terminal value for pressure. Where appropriate, step (a) comprises providing an array of pressure sensors.

Optionally, step (c) of the method comprises substeps: step (c1)—selecting a plurality of neighboring pressure sensors from the array; and step (c2)—acquiring at least one pressure value measured from each member of the plurality of neighboring pressure sensors.

Optionally, step (d) of the method comprises substeps: step (d1)—calculating a best-fit value of the time-constant for at least a selection of pressure sensors from the plurality of neighboring pressure sensors; step (d2)—taking a mean value of the time-constant values calculated for the selection of pressure sensors.

In still another embodiment, a method is disclosed for monitoring amplitude of an alternating current signal in a pressure sensing system by: collecting a plurality of current signal outputs during a time period T of the alternating current signal; obtaining a signal profile for the duration of the time period T; identifying a maximum-peak current signal output; identifying a minimum-peak current signal output; and calculating the current difference between the maximum-peak current signal output and the minimum-peak current signal output for use in determining a pressure exerted upon the pressure sensing system. Optionally, the current difference may be multiplied by a factor of $1/\sqrt{2}$.

Where appropriate, the samples are taken at discrete time intervals δt. Optionally, δt is smaller than T such that the cycle-to-sample ratio T/δt is greater than one. Accordingly, the cycle-to-sample ratio T/δt may be selected such that a plurality of samples are taken within each cycle. In certain embodiments, the cycle-to-sample ratio T/δt is within the range 10 to 1000, possibly with δt≈$10^{-6}$ seconds and T≈$10^{-5}$ seconds. Optionally, the method may exclude current output values outside of a tolerance level of current output values.

In another embodiment a method is disclosed for selecting an optimal gain level for amplifying an input signal in a pressure sensing system having a plurality of sensors, the method comprising: providing a variable gain amplifier having an input and an output; determining a saturation level for the amplifier: sampling the input signal; determining a peak value of the input signal; and selecting an optimal gain level equal to or less than the ratio of the saturation level to the peak value for use in determining a pressure exerted upon the pressure sensing system. Optionally, the step of sampling the input signal comprises processing the input signal with an analog to digital converter.

Where appropriate, the step of determining a peak value of the input signal comprises: selecting a maximum value and an output value of an output signal from the analog to digital converter; and calculating the difference between the maximum value and the minimum value.

Accordingly, the method may further comprise: (a) initializing a gain level for each of the plurality of sensors; (b) aggregating sensors into sets of sensors requiring a common gain level; (c) obtaining analog readings from the sensors in each set; (d) amplifying the analog readings from the sensors of each set according to the gain level associated therewith; (e) calculating a new gain value required for each sensor; and (f) repeating steps (b) to (e).

Optionally, the method further comprises: selecting an initial gain level for the amplifier; the plurality of sensors each sending an analog signal to the input of the variable gain amplifier; the variable gain amplifier amplifying the input signal by the initial gain level; sampling the output of the variable gain amplifier with an analog to digital converter; communicating a digital output signal from the analog to digital converter to a controller unit; the controller unit determining peak to peak value of the digital output signal; and the controller using the peak to peak value to calculate an optimal gain level for the amplifier.

According to another embodiment, a pressure sensing system is disclosed comprising: a sensing apparatus comprising an array of n capacitors each formed at the intersections of a plurality of linear conductor columns and a plurality of linear conductor rows, and wherein the columns and rows are respectively disposed on opposite sides of a sheet of a compressible dielectric; and a controller configured to derive capacitance values for each capacitor and determine a pressure exerted upon the sensing apparatus.

Optionally, the controller may be operable to apply an alternating known voltage to n circuits, each of the n circuits comprising a different bank of n−1 capacitors connected in parallel and one remaining capacitor connected in series with the bank.

Where appropriate, the controller is further operable to measure the alternating current of each of the n circuits thereby deriving total capacitance of each circuit from the known voltage and measured current. Accordingly, the controller may be operable to apply an alternating known voltage to an n+1 circuit comprising n capacitors interconnected in parallel and to measure the alternating current of the n+1 circuit and thereby to derive the total capacitance of the n+1 circuit.

Additionally or alternatively the controller may comprise at least one variable gain amplifier and at least one analog-to-digital converter. Optionally the variable gain amplifier is operable to amplify at least one analog signal with an associated gain level. Accordingly, the controller may be operable to receive digital output signals from the analogto-digital converter and to calculate an optimal gain level for associated analog input signals.

Optionally the controller is operable to monitor amplitude of an alternating current signal by collecting a plurality of current signal outputs during a time period T of the alternating current signal; obtaining a signal profile for the duration of the time period T; identifying a maximum-peak current signal output; identifying a minimum-peak current signal output; and calculating the current difference between the maximum-peak current signal output and the minimum-peak current signal output.

Where appropriate, the controller may be operable to determine a terminal value for a parameter being monitored by the controller by providing a mathematical model for the behavior of the parameter over time, the model comprising a formula expressing a relationship between the parameter and at least one variable; monitoring the parameter; acquiring a plurality of measured values for the parameter over time; calculating a best-fit set of values for the at least one variable based upon the plurality of measured values for the parameter; and using the best-fit set of values and the formula to determine a predicted terminal-value of the parameter.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of embodiments of the present invention, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice. In the accompanying drawings.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Detection systems and methods are described hereinbelow which may be used for example to monitor the pressure exerted upon a patient so as provide feedback directed towards preventing the development of pressure wounds.

A pressure sensing system includes a pressure detection mat comprising a layer of insulating material sandwiched between a first conductive layer and a second conductive layer. Each conductive layer may comprise parallel strips of conductive material. Such a system is described in the applicants' copending international patent application WO 2010/119441, which is incorporated herein by reference.

WO 2010/119441 discloses a pressure sensing mat which may be placed between a seat of a chair or under a bed mattress and the body of a prone subject so as to monitor the pressure exerted upon the subject. The output of the pressure sensing mat may be used to indicate the risk of pressure-wound development.

Figure 1A:
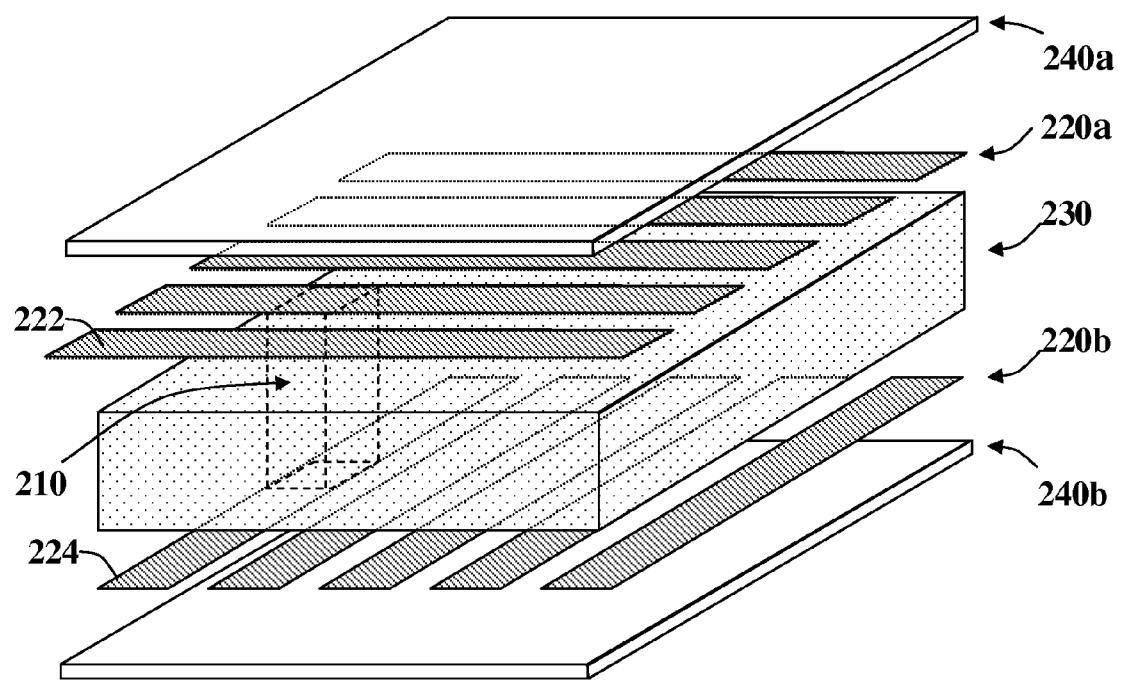
FIGS. 1a-d show various isometric projections of embodiments of a pressure-detection mat.

Reference is now made to FIG. 1a showing an isometric projection of an embodiment of a pressure-detection mat 200 comprising a plurality of sensors 210 arranged in a form of a matrix. The mat may include two layers 220a, 220b of conductive material separated by an insulating layer 230 of isolating material. Each of the conductive layers may comprise parallel conductive strips 222, 224 and the two conductive layers are arranged orthogonally such that in one conductive layer the strips are horizontal 222 and in the other conductive layer they are vertical 224. Each strip is wired to a control unit and may be operable by safe low voltage source.

A capacitance sensor is based on the capacitance between the sections of the conducting strips overlapping at each "intersection" of a vertical conductive strip with a horizontal conductive strip. These capacitance sensors are configured such that pressing anywhere on their surface changes the spacing between the two conductive layers, and consequently the capacitance of the intersection. A driving unit may selectively provide an electric potential to the vertical strip and the electrical potential may be monitored on the horizontal strip such that the capacitance sensor of the overlapping section may be determined.

It is noted that by providing an oscillating electric potential across each sensor and monitoring the alternating current produced thereby, the impedance of the intersection may be calculated and the capacitance of the intersection determined. Thus, where the mechanical properties of the sensor are known, the pressure exerted upon the sensor may be deduced.

The mat may further include additional sensors configured to monitor additional factors, particularly additional factors influencing the development of bedsores, such as temperature, humidity, or the like. Such additional sensors may be configured to monitor the factors continuously or intermittently as appropriate to detect high risk combinations of factors. Such measurements may be recorded and stored in a database for further analysis.

In certain embodiments of the pressure-detection mat, the materials are selected such that the conductive layers and insulating layers are flexible. The insulation material may be a compressible sponge-like, airy or porous material (e.g. foam), allowing for a significant change in density when pressure is applied to it.

The pressure-detection mat 200, or sensing-mat, may be placed underneath or otherwise integrated with other material layers 240a, 240b such as used in standard bed sheets. It will be appreciated that such additional materials may confer further properties as may be required for a particular application. In one embodiment, the conductive material of the sensors may be wrapped by isolating, water resistant, breathing cover mat, allowing minimum discomfort to the subject resting on the mat.

Figure 1B:
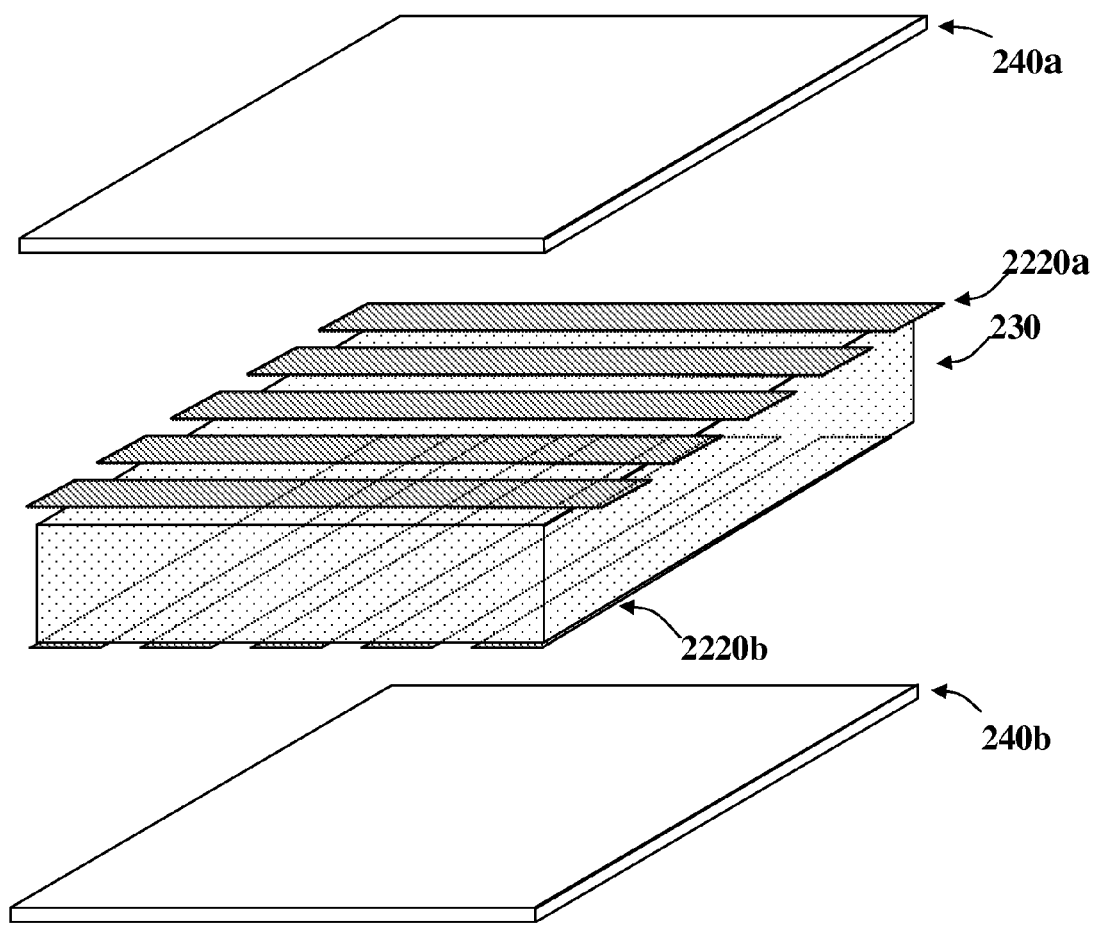
Figure 1C:
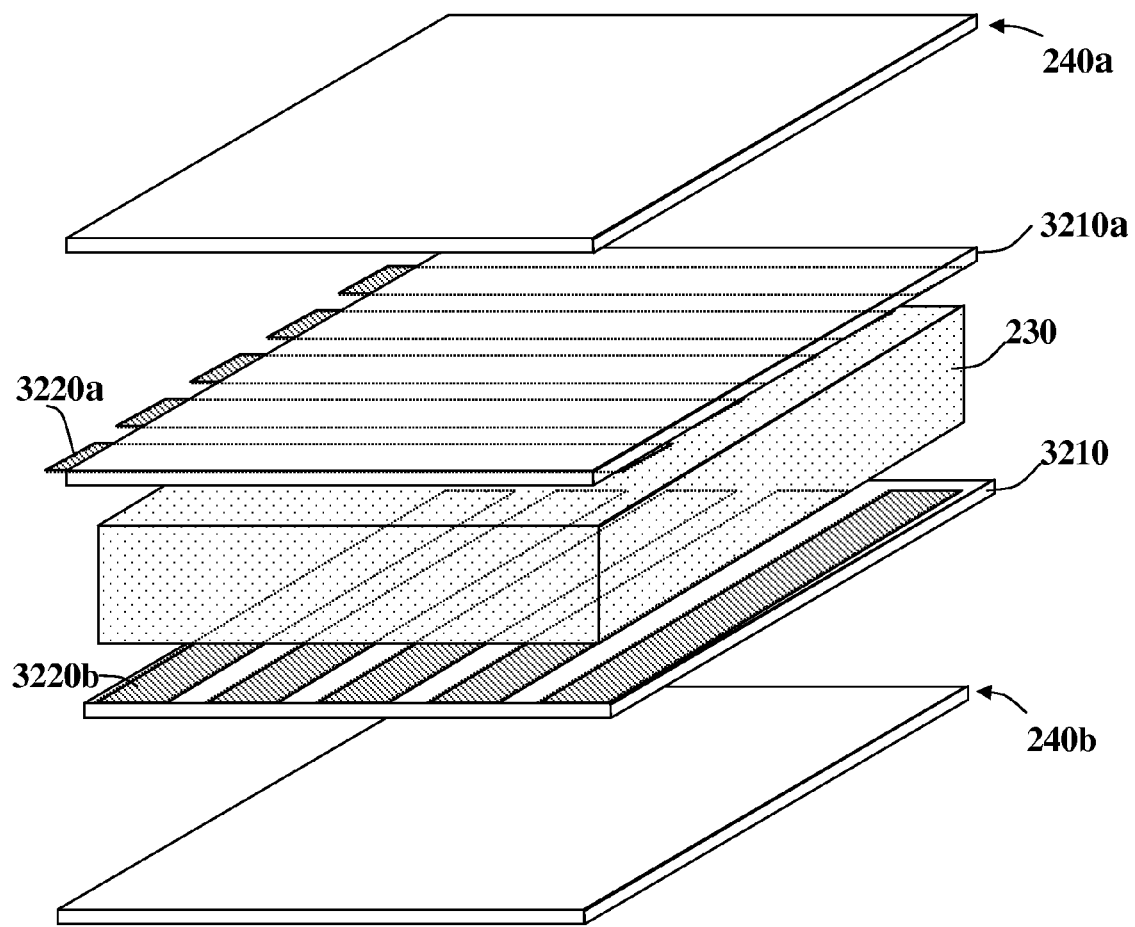
Figure 1D:
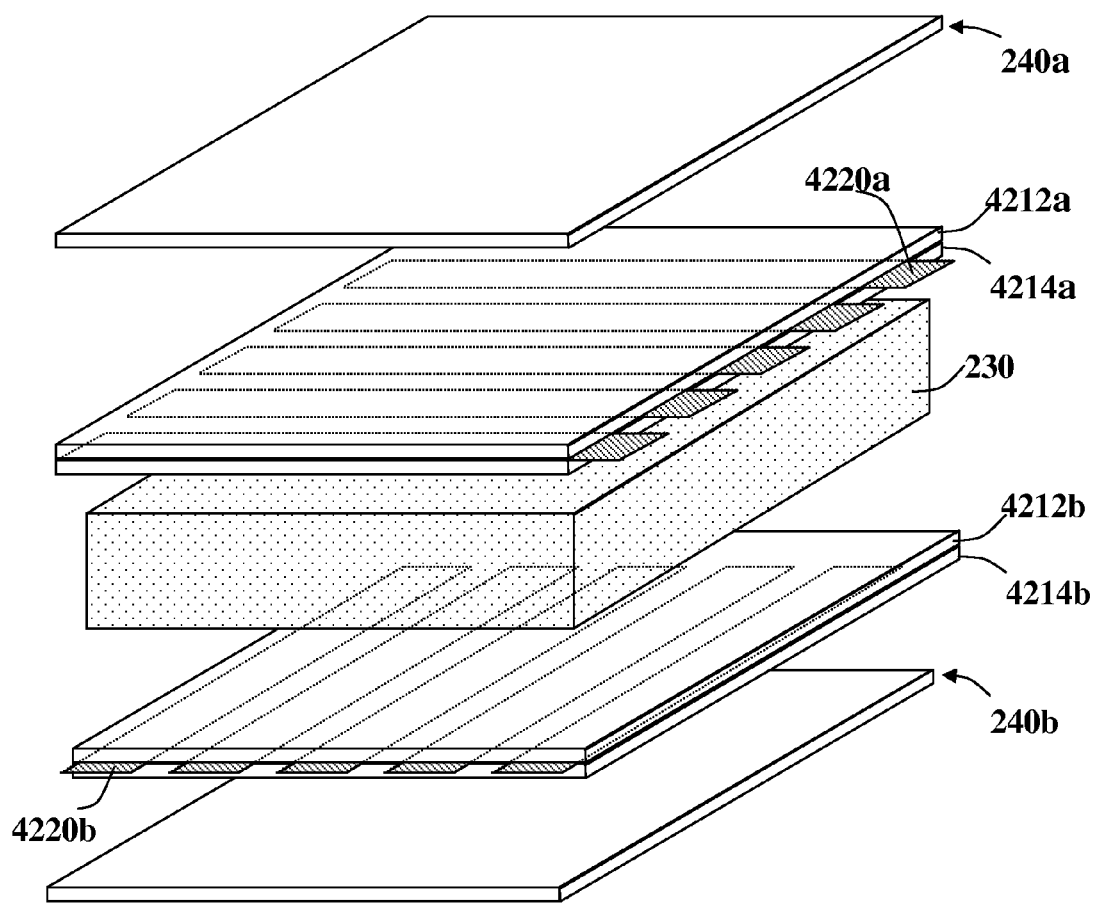

With reference now to FIGS. 1b-d showing various sections of various embodiments of the pressure-detection mat, the conductive layers 220 (FIG. 1a) may be supported by various substrates. For example FIG. 1b shows two conductive layers 2220a, 2220b adhered directly to the insulating layer 230. Alternatively, as shown in FIG. 1c, conductive layers 3220a, 3220b may be supported by separate substrates 3210a, 3210b, such as of TPU for example, the insulating layer 230 being sandwiched therebetween. In still another embodiment, as shown in FIG. 1d, the conductive layers 4220a, 4220b may themselves each be sandwiched between two substrates 4212a, 4214a, 4212b, 4214b respectively.

Figure 2:
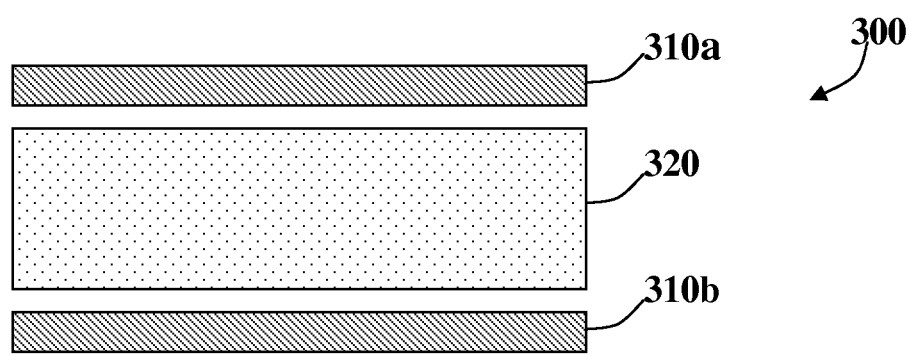
FIG. 2 shows a cross section of an embodiment of a single sensor.

Reference is now made to FIG. 2, showing a cross section of an embodiment of a single sensor node 300. In this embodiment, the sensor is a capacitor comprised of two layers of conductive strips 310a, 310b and an insulating layer 320 of isolating material therebetween. Pressing anywhere on the sensor would compress the insulating layer 320 changing the distance between the conductive strips and thereby changing the capacitance of the capacitor.

It will be appreciated that in order to get a stable reading of impedance values from a row of sensors, it is preferable that little or no movement be made by the subject during the taking of readings from the sensors. Accordingly, according to certain embodiments the time taken for readings may be of the order of tens or hundreds of milliseconds, during which movement of the subject is generally insignificant. It will be further appreciated that in applications where the subject is largely immobile, it may be desired to use longer reading times as required.

Capacitance Measurement

The parallel strips of the first conductive layer and the parallel strips of the second conductive layers overlap at a plurality of intersections which are referred to as nodes. The first conductive layer and the second conductive layer may be configured such that the parallel strips of the first conductive layer are arranged orthogonally to the parallel strips of the second conductive layer but other embodiments have various other relative orientations. The nodes form capacitance sensors.

Reading capacitance values using a matrix of nodes reduces the number of wires required in comparison to the number required when using a single capacitor for each node. However, when using matrix readings all the nodes of a measured row or column are interdependent, which may lead to interfering stray capacitance. Therefore some kind of calibration of the capacitance measurements is typically required.

The methods and system disclosed herein do not require the addition of a reference capacitor to each row. The currently disclosed systems are therefore simpler, quicker and more cost effective than the systems described by Altman et al. in US2009/0216466.

A line of capacitors may constitute a group of capacitors connected in parallel, in which case the total capacitance of the row will be the sum of the capacitances of the capacitors in the row. Alternatively, the capacitors may be connected in series, in which case the total capacitance of n capacitors will be:

$$C_t = \frac{1}{\frac{1}{C_1} + \frac{1}{C_2} + \ldots \frac{1}{C_n}} \quad [1]$$

A circuit with a capacitor C through which an alternating current (AC) passes has the following root mean squared current $I_{ac}$:

$$I_{ac} = 2\pi f C V_{ac} \quad [2]$$

Where f is the frequency of the current alternation, and $V_{ac}$ is the root mean squared value of the AC voltage.

The capacitance is thus:

$$C = \frac{2\pi f V_{ac}}{I_{ac}} \quad [3]$$

By monitoring $V_{ac}$, $I_{ac}$ for the given AC frequency f, the capacitance may be determined.

Figure 3A:
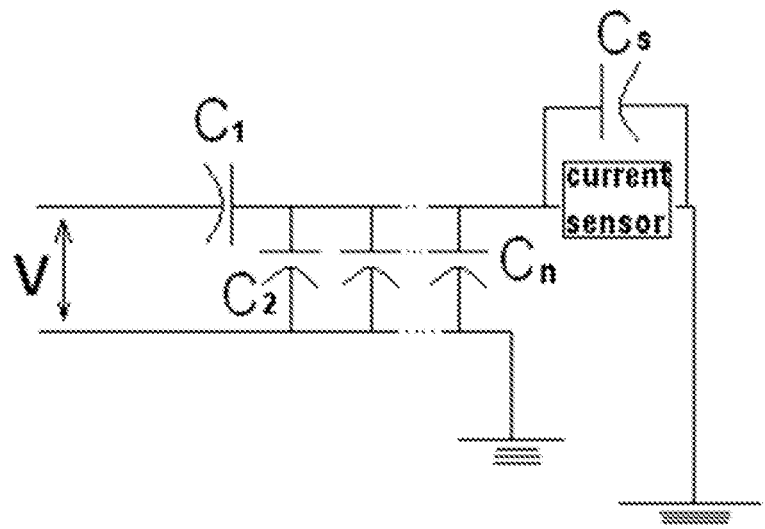
FIG. 3a shows a circuit for measurement of total capacitance from a group of capacitors in which one capacitor is connected in series to an array of capacitors connected in parallel.

FIG. 3a shows n capacitors $C_{1-n}$ arranged in a circuit along with a current sensor. In the absence of stray capacitance $C_s$ the capacitances of each of the n capacitors may be determined by applying voltage V as shown and measuring the current. The total capacitance $C_T$ of the circuit, were there no stray capacitance, would be:

$$\frac{1}{C_T} = \frac{1}{C_1} + \frac{1}{C_2 + C_3 + \ldots C_n} \quad [4]$$

n equations such as the above, but with each having a different measured $C_T$, would suffice to determine the capacitance of all capacitors. Thus current measurements may be taken for each of n circuits, where in each circuit a different capacitor of the n capacitors is in turn selected to be connected in series with the parallel array of all the other capacitors.

In practice, where stray capacitance is a factor to be considered, although relative values of capacitance may be thus determined, n such equations are insufficient to obtain absolute capacitance values.

Without wishing to limit the invention to theory, it is possible that the stray capacitance may be a large contributor to the circuit's total capacitance thereby effecting the total capacitance calculation. In order to find absolute capacitance values a reference capacitor of known value may be added but this approach may be undesirable.

Figure 3B:
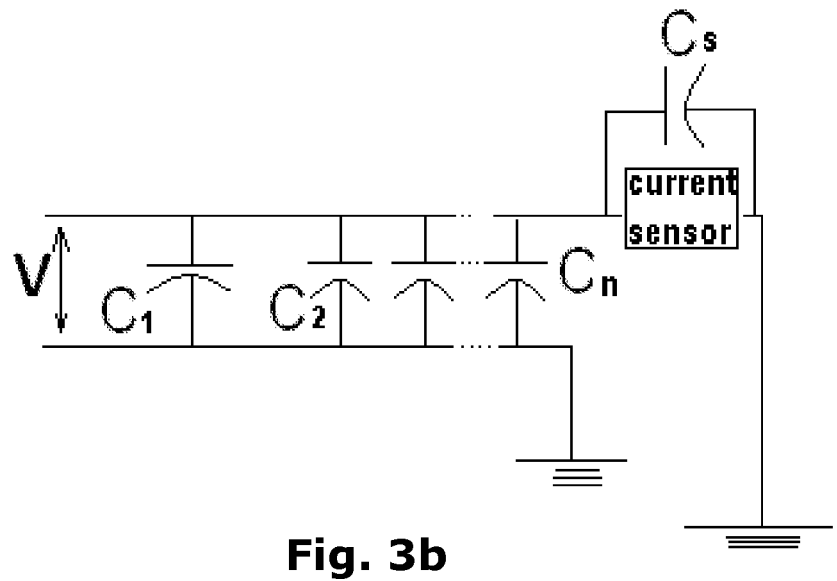
FIG. 3b shows a circuit for measurement of total capacitance from a group of capacitors connected in parallel.

It has surprisingly been discovered that measuring the total capacitance from the additional circuit shown in FIG. 3b, obviates the need for a reference capacitor to measure the capacitances in presence of a large stray capacitance. The total capacitance of the circuit of FIG. 3b is given by the additional equation:

$$C_T = C_1 + C_2 + \ldots + C_n + C_s \quad [5]$$

This provides an additional equation which may be used to calculate absolute capacitance values without redress to the use of a reference.

The mapping may further comprise measuring the total capacitance of each row with an unloaded mat (i.e. zero pressure, no subject is applying pressure to the mat) to calibrate the pressure-capacitance relationship.

Alternatively or additionally, calibration of the system may further comprise loading each row with a "standard" heavy load and concomitantly measuring the total capacitance of each row.

Mapping of the pressure may further comprise continuously or repeatedly mapping capacitance over time from the same array, at least as long as a subject is on the mat. The dynamics of the distribution of pressure may be monitored and analyzed, for example medical personnel may use the results of measurement of changes or rate of changes of pressure at nodes to help identify, predict or prevent problem regions, or progress and improvement.

The embodiments generally provide a caretaker or an active system with indications of pressure distribution and ongoing, accumulated pressure exerted upon body parts of a subject on the mat, which may result in the creation or progression of a bedsore. A caretaker or active system may then take proper action. Embodiments of the system may also be used for ongoing analysis and recording of a subject's care routine.

Data Analysis and Display

A software application may be used to retrieve data from at least one data storage unit, analyze it for various purposes, and display the analysis results in various formats to a user. The software application may further include features such as, but not limited to analyzing indications of shear forces by comparing relative pressures detected by adjacent pixels, presenting pressure as detected by the different sensors on one or more pressure-detection mats, and alarming a user that a subject is prone to develop a pressure wound in a specific body part.

External wounds caused by tissue breakdown may develop into pressure wounds, over time. Shear forces are a common cause of such tissue breakdown. Software may further be used to analyze data received from the pressure detection mat to determine whether shear forces are exerted upon body parts of a subject. Where a subject rests upon the mat, two adjacent sensors are expected to measure approximately similar pressure levels. If that is not the case, the software deduces that the subject is sliding upon the sensing mat and shear forces are possibly exerted upon the subject's body, creating tissue breakdown.

Data analyzed from a pressure detection mat may be presented to at least one of a care-giver, a nurse, a man-monitored station, a friend or family member of the subject, to the subject himself or any relevant party. The display unit used to present data may be, for example and without limitation, one or more of computer screens, laptops, PDAs, cellular phone screens, printed sheets, and integrated LCD screens (e.g. TFT, touch screens).

Displaying data to more than one monitor, for example both to a family member and a hired caretaker of a subject, may assist in verification that the subject is receiving proper care from his caregiver. Displaying data to the subject himself is particularly useful in paraplegic subjects who have partial mobility. For example, a subject paralyzed from the waist down and sitting in a wheelchair may not be able to sense that a pressure wound is forming on his abdomen. However, using the pressure wound prevention system; he can receive a notification that accumulated pressure has been detected where his abdomen typically rests. The subject may then lean his hands on the wheelchair's arm rests and lift his abdomen off the wheelchair seat for several seconds, thus relieving pressure off the sensitive area.

Data display may include alarms. Alarms may be vocal, visual, tactile, or the like. Presentation of the alarms may be 'local' to the subject himself or 'remote' when presented to one or more users typically in charge of a subject's care, such as but not limited to a family member or a nurse at a monitoring station.

The system may further be configured to include components capable of sending data regarding the system's whereabouts, using a global positioning system (GPS) or other tracking technologies as suit requirements. For example, data such as pressure-wound formation alerts may be sent along with the system's location to a manned monitoring station. This capability may be useful, for example, when data is sent to a caretaker in charge of multiple subjects who use wheelchairs for mobility within a hospital, a nursing home or another care environment. This information can assist the caretaker in finding the subject within the care facility he resides in and provide him with proper care.

It will be appreciated that the system as described hereinabove may be particularly useful in care facilities such as, amongst others, acute care facilities, sub-acute care facilities, long term care facilities, home care environments, hospices, hospitals, nursing homes, assisted living facilities and the like. In addition similar systems may be adapted for use in other environments such as hotels, vehicle seats, passenger seats, airplane seats, long-haul flight seats and the like.

Rapid AC Sampling

Capacitance measurements from the sensors are translated into pressure readings. Information received from the sensors is analyzed by the system, which further issues alerts according to sensor readings.

Referring back to equation [2], alternating current measurements like those used in such capacitance sensors may be determined according to amplitude measurements of the alternating current. Various methods for determining the amplitude of alternating current may be used. For example, one approach is to rectify an alternating current to a direct current, and measure the direct current instead of the alternating current. Another approach is to add a resistor and measure the heat generated from the resistor, or an Analog to Digital converter which compares an analog signal to a series of predefined voltage references and returns the respective digital signal representing the voltage value.

These known methods may require more than one cycle of an AC signal in order to acquire accurate readings of the alternating current amplitudes. This may not be an option when continuous measurements are required or when alternate current amplitudes change at relatively high rates.

Embodiments of a method for quick measurement of an alternating current (AC) signal amplitude are disclosed herein which may be applicable for use in a sensing mat such as described above comprising pressure-detection sensors arranged in a matrix. It will be appreciated that the method for rapid measurement described below may also be applied to other systems in which rapid AC recordation is required.

According to the sensing mat embodiment, each pressure-detection sensor monitors the capacitance between layers of conducting material. A layer of insulating material is sandwiched between two conductive material layers. Each sensor is configured such that pressing anywhere on its surface changes the spacing between the two conductive layers, and consequently the capacitance of the sensor.

The insulation material may be a compressible, sponge-like, airy or poriferous material (e.g. foam), allowing for a significant change in density when pressure is applied to it. Pressure applied upon a sensor affects the distance between the two conductive layers, thus changing the capacitance of the sensor. Consequently, by measuring the amplitude of an alternating current running through such a sensor, one can calculate the sensor's capacitance and deduce the pressure applied upon that sensor from the calculated capacitance.

The amplitude of AC current depends upon the impedance of the circuit. There is an inverse relationship between capacitance and impedance. As pressure is applied to the sensor the plates of the capacitor are pressed closer together increasing the capacitance. In response, the amplitude of the current tends to increase. The increased amplitude may be measured by monitoring the AC amplitude for example, as described below. The sooner that changes in the current signal are identified, the shorter the response time of the sensor.

It should be further noted that the variation of sensor alternating current readings over the duration of the response time may be modeled mathematically. For example, when there are no significant pressure changes, the AC current signal values may be as shown in FIG. 4a, showing a graph which represents current changes over time in response to an alternating current running through a pressure sensor.

Figure 4A:
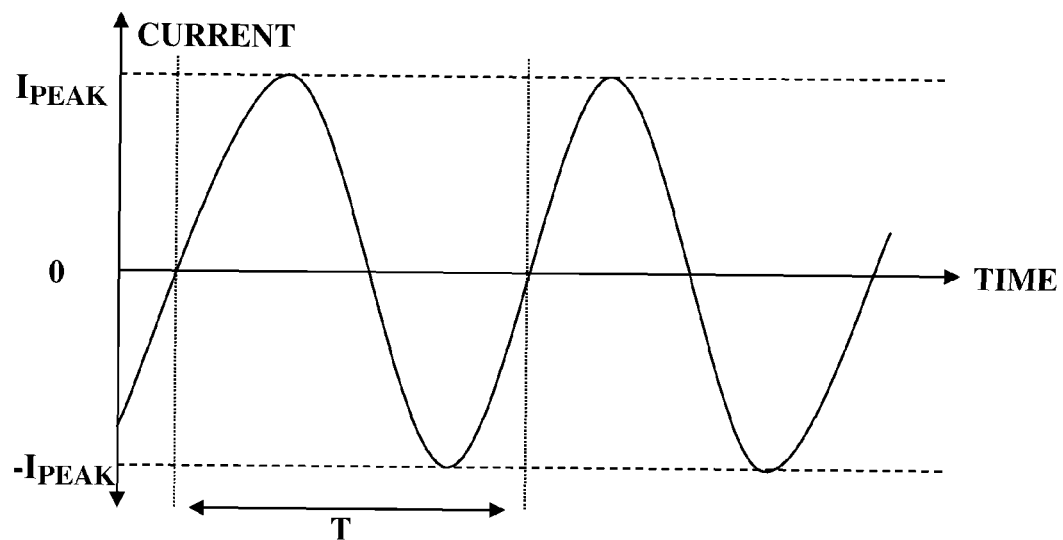
FIG. 4a is a graph representing current changes over time in response to an alternating current running through a pressure sensor.

Referring to the graph of FIG. 4a, showing the variation of current over an AC cycle, the graph represents a relatively consistent AC signal with fixed amplitude. This profile may represent the current measured by a sensor when no pressure changes are made during the cycle. In the graph, T represents a time period of a single AC cycle, $I_{peak}$ represents the maximal current reading and $-I_{peak}$ represents the minimal current reading.

Figure 4B:
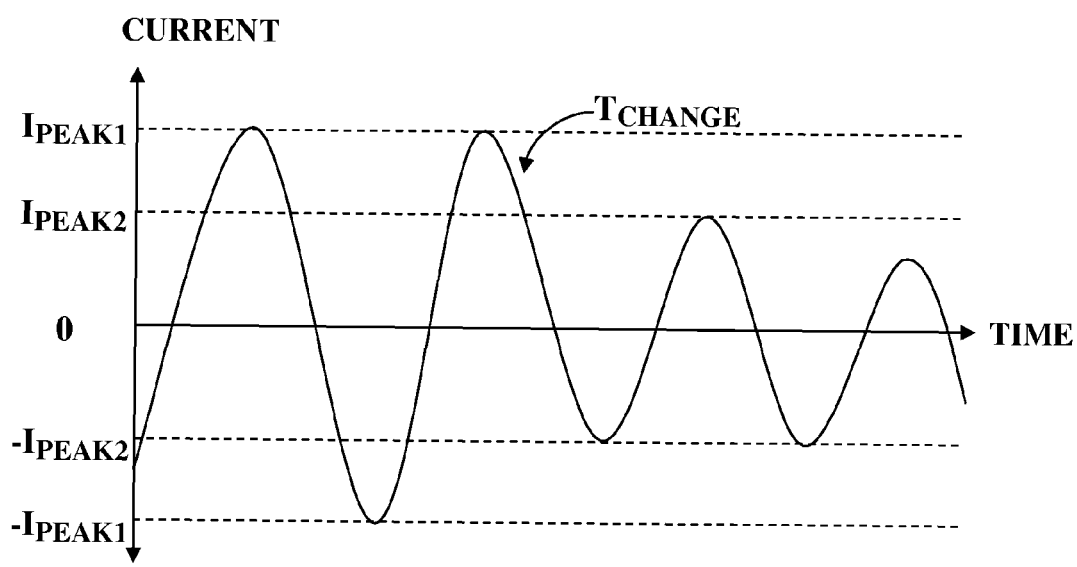
FIG. 4b is a graph representing current changes in response to changes made to pressure applied on a pressure sensor.

When the pressure level exerted upon a sensor changes, the capacitance of the sensor changes accordingly, and with it the AC signal amplitude. This is represented graphically in in FIG. 4b. Referring to the graph of FIG. 4b, at time the moment of change $T_{change}$ the AC signal amplitude becomes smaller. Accordingly, the peak values (minimal and maximal current readings) of the AC signal amplitude vary. Note that in this sample, the absolute peak values of the current readings after the moment of change $T_{change}$ are significantly lower than those measured before $T_{change}$ so $|I_{peak2}|<|I_{peak1}|$.

As described above, using standard measuring techniques, more than one cycle may be needed to acquire accurate readings of alternating current amplitudes. In cases where this is an option, such as the sensing-mat sensors, pressure changes may affect the alternating current amplitudes at relatively high rates. In one embodiment, the method described hereinbelow may determine the amplitude of alternating current with a short response time, even within a single cycle.

The method is based on a plurality of current signal samples taken during one or more alternating current cycles. The time interval T will be referred to herein as the time period of a single AC cycle.

AC signal samples may be obtained, for example and without limitation, using a high speed Analog to digital converter (ADC). AC signal samples may be obtained at various frequencies. For example, the AC signal may run at a rate of 100 kilohertz, and the current signal samples may be obtained at a rate of 3 Megahertz, such that 30 current samples may be obtained within one AC cycle.

Samples are generally collected at fixed time intervals δt. Accordingly, the cycle-to-sample ratio is T/δt. According to an embodiment of the rapid AC current monitor described herein, the cycle-to-sample ratio may be large. In some embodiments, the cycle-to-sample ratio may be within the range, 10-1000 although other values may be selected as suit requirements so as to sample the varying current as outlined herein.

Figure 5:
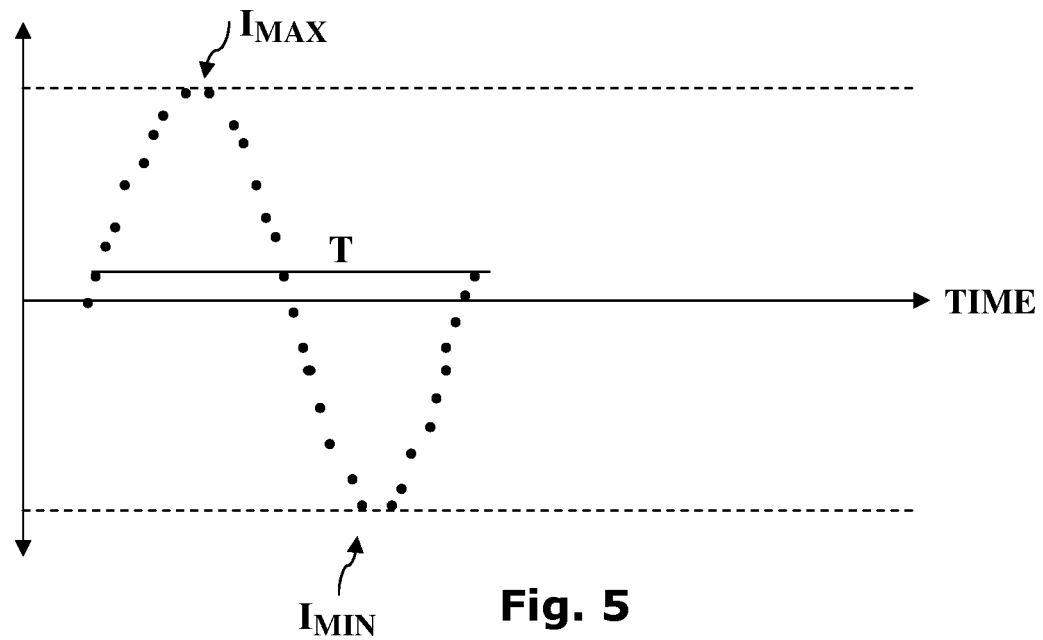
FIG. 5 illustrates a plurality of signal readings over a time period T of a single AC cycle.
Figure 6:
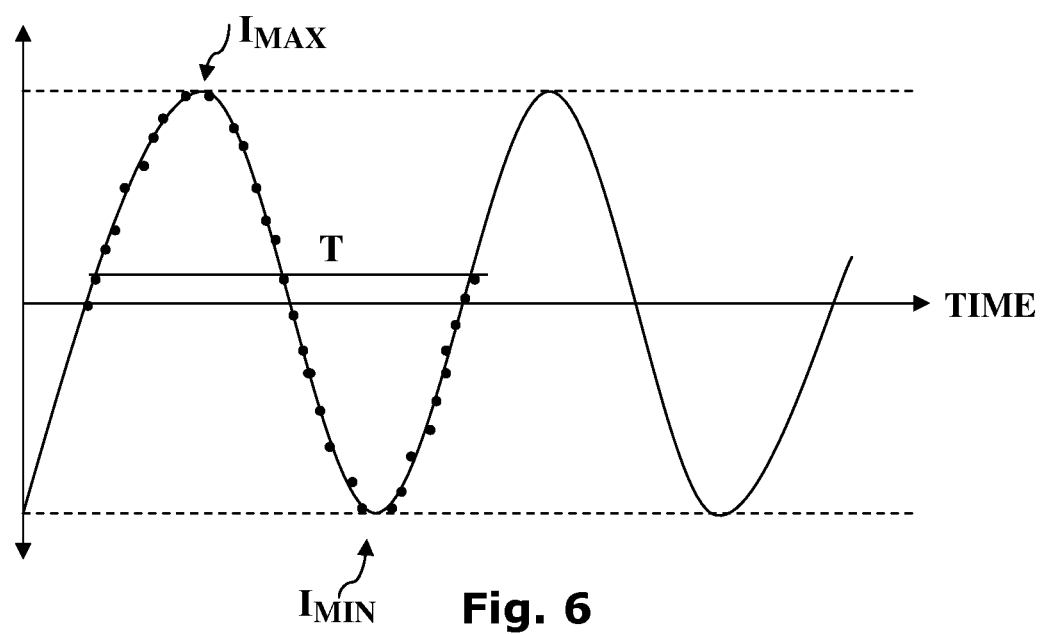
FIG. 6 illustrates an AC profile obtained from a plurality of signal readings.

FIG. 5 illustrates a plurality of signal readings over the time period T of a single AC cycle. Such signal sample readings may be analyzed to obtain a signal profile such as shown in FIG. 6. It will be appreciated that not all AC signal representations appear as smoothly as shown in the graph of FIG. 6. Moreover, in some cases, discrete samples with extreme values, lying outside a tolerance level, may get discarded in order to create a signal profile.

Current level may be determined by identifying the minimum current $I_{max}$ and maximum current $I_{min}$ of the profile. By calculating the current difference between these peak values $I_{max}$, $I_{min}$, the amplitude of the AC signal may be identified.

In the specific case of a pressure sensor of the sensing mat, once the amplitude is determined, the capacitance of the sensor can be calculated and the pressure applied upon the sensor can be deducted, optionally using techniques described herein.

Figure 7:
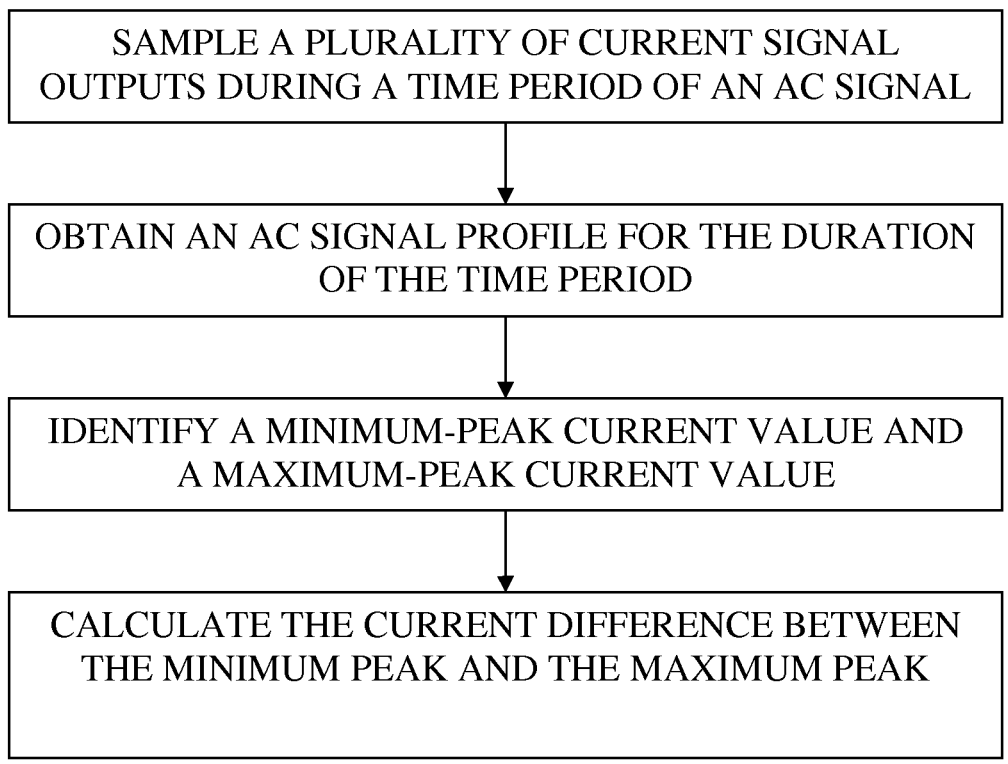
FIG. 7 illustrates a flow chart of a method to determine an amplitude of an alternating current during the course an AC cycle.

Reference is hereby made to FIG. 7, illustrating a flow chart of the method to determine an amplitude of an alternating current during the course of one or more AC signal cycles. The flow chart illustrates sampling a plurality of current signal outputs during a time period of an AC cycle and obtaining an AC signal profile for the duration of the time period. Optionally, some out-of-range values will be discarded prior to determining the signal profile according to the readings.

The method continues with identifying the minimum and maximum peak values of the signal outputs, possibly using extrapolation, selection or the like. These may be used in calculating the current difference between the minimum and the maximum peak values to determine the amplitude of the AC signal.

It will be further appreciated that, where an absolute current value is required a root-mean-square (RMS) value may be taken by dividing the peak to peak value by $\sqrt{2}$.

Terminal Value Prediction

A further technique which may be used to obtain rapid data from sensors may be applied to sensors with long response times. The technique may involve predicting a terminal-value of a parameter from a small sample of initial values. The technique will be demonstrated through reference to the example of a sensing mat comprising pressure-detection sensors which may be arranged in a matrix, such as described above.

According to the sensing mat embodiment, each pressure-detection sensor monitors the capacitance between layers of conducting material. A layer of insulating material is sandwiched between two conductive material layers. Each sensor is configured such that pressing anywhere on its surface changes the spacing between the two conductive layers, and consequently the capacitance of the sensor.

The insulation material may be a compressible, sponge-like, airy or poriferous material (e.g. foam), allowing for a significant change in density when pressure is applied to it. In one embodiment, the insulation material's response to pressure is continuous, and it may require a significant response time for the pressure reading from the sensor to stabilize at a terminal value.

It is noted that the variation of sensor readings over the duration of the response time may be modeled mathematically. For example, the response of a sponge based pressure sensor may be expected to vary exponentially. It is a particular feature of embodiments described herein that the mathematical model of response variation may be used to predict the expected final value for the sensor reading.

Figure 8A:
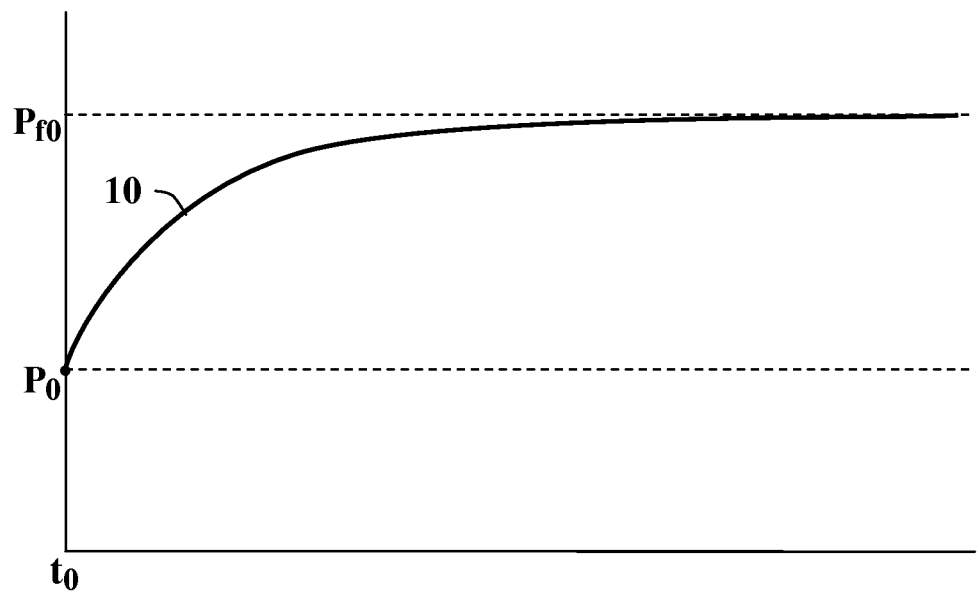
FIGS. 8a-c illustrate a series of graphs showing possible mathematical models for a sensor response associated with a pressure sensor.

Referring now to FIG. 8a, a graph is presented showing a possible exponential model for the sensor response associated with a pressure sensor such as described above. The X axis represents time elapsed and Y axis represents pressure readings of a sensor. The graph illustrates the expected pressure readings which would be recorded by a pressure sensor in response to a pressure change at time $t_0$.

The model for the behavior of the parameter may be provided by a mathematical formula expressing the relationship between the behavior of a parameter such as the pressure response and time elapsed from the moment a change in pressure has occurred. A typical formula could contain an exponential relationship, and may be, for example and without limitation:

$$P=(P_F-P_0)(1-e^{(t-t_0)/\tau})+P_0$$

where:
$t_0$ represents the time at which pressure change occurred
$P_0$ represents the pressure reading value at time $t_0$
t represents the time at which a sample reading was taken
P represents the pressure reading from the sensor at time t
$P_F$ represents the estimated terminal pressure reading value
T represents the time constant of a particular sensor.

The above formula may enable a user, a computer or some other computing device to predict a value for the terminal pressure reading $P_F$ given a particular value for τ and pressure readings P and $P_0$ at times t and $t_0$ respectively. The value for τ may obtained by measurement or estimation as required.

The mathematical model may reflect the behavior of a parameter in response to changes in one or more variables. In the pressure-sensor sample, the model illustrates how the pressure reading parameter behaves over time, alternatively, a more complex mathematical formula may be used to model how the pressure reading behaves in response to more than one variable. For example, models may be developed predicting the behavior of the pressure reading parameter in response to changes in temperature, ambient pressure, humidity or the like over time.

According to requirements, variable values such as changes to air temperature may be controlled by a user or a control system. Alternatively, some variables may be uncontrolled but measured, such as the elapsed time from a pre-defined event.

Figure 8B:
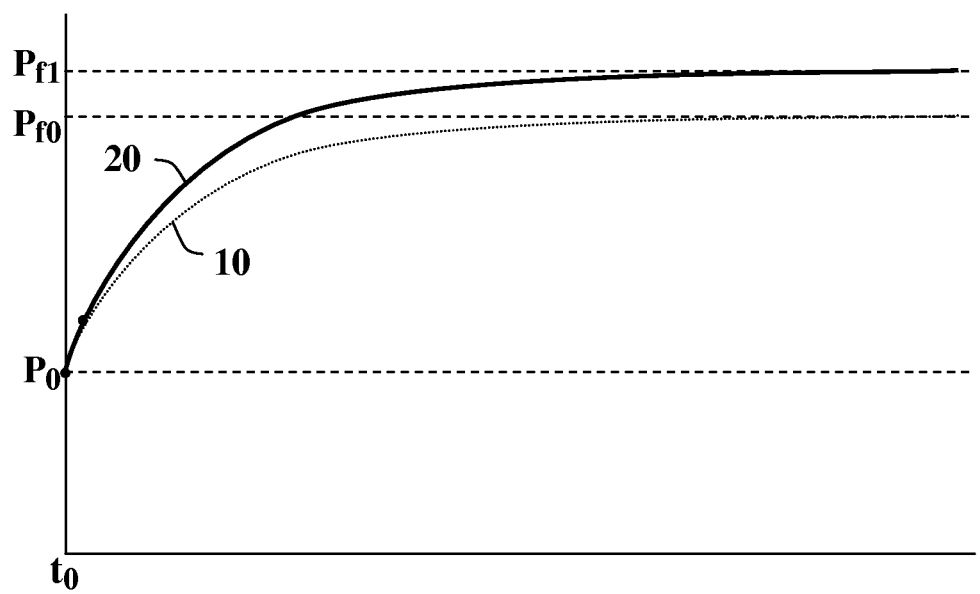
Figure 8C:
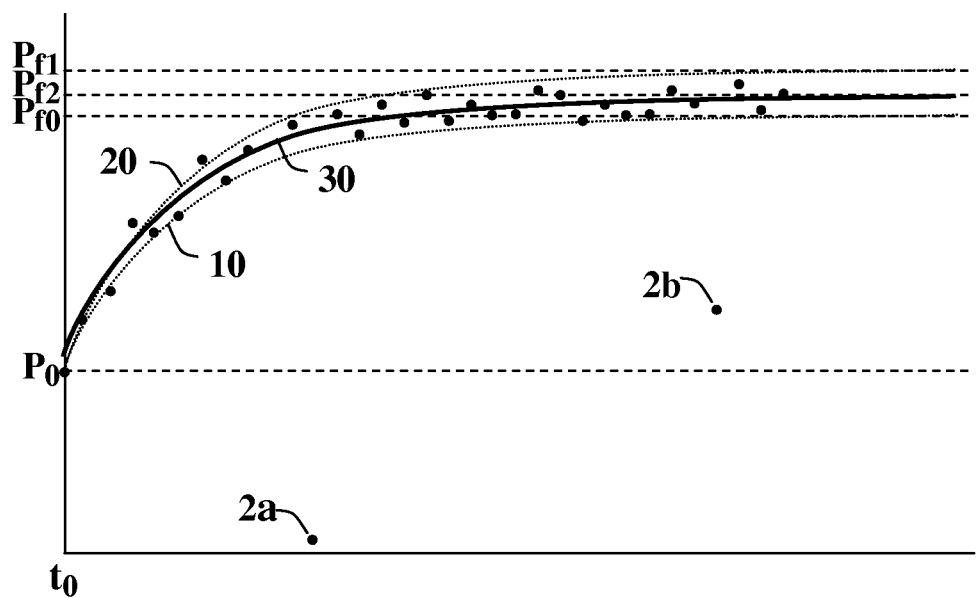

The series of graphs represented in FIGS. 8a-c show how the mathematical model may be determined and adjusted to suit actual recorded values over time. With particular reference to FIG. 8a, an initial pressure reading $P_0$ is recorded by a sensor at time $t_0$.

A formula such as the one above may be determined initially using a first-estimate value for the time constant variable τ. The first-estimate value may be selected using a number of methods, such as calculating a value based upon the last set of samples recorded, calculating the value of the time constant during a calibration or initialization procedure, using a manufacturer's recommended value or the like.

The first-estimate value for the time constant τ may be used to calculate a first predicted terminal value of the pressure reading $P_{f0}$. The initial model is represented on the graph of FIG. 8a by the initial prediction line 10.

Referring now to FIG. 8b, a second graph is represented after two samples have been recorded. The two samples may be used to provide an updated estimate for the value of the time constant variable τ, for example using some approximation techniques such as the method of least squares or the like. Using the new estimated time constant variable τ, an updated predicted terminal value of the pressure reading $P_{f1}$ may be calculated. The updated model is represented on the graph of FIG. 8b by an updated prediction line 20.

The graph of FIG. 8c shows a further updated mathematical model following a plurality of recordings. It is noted that the multiple recorded pressure values may be used to produce a better estimate of the time constant variable τ such that an improved predicted terminal value for the pressure reading $P_{f2}$ may be calculated. This is represented on the graph of FIG. 8c by the line of best fit 30. It is noted that recorded values 2a, 2b which vary significantly from the predicted behavior of the parameter, may be discarded from estimation calculation.

It is noted that all the predictive graphs 10, 20 and 30 all obey the mathematical formula:

$$P=(P_F-P_0)(1-e^{-(t-t_0)/\tau})+P_0$$

Differences between the three lines are due to differing estimations of the time constant τ used for each model.

Figure 9:
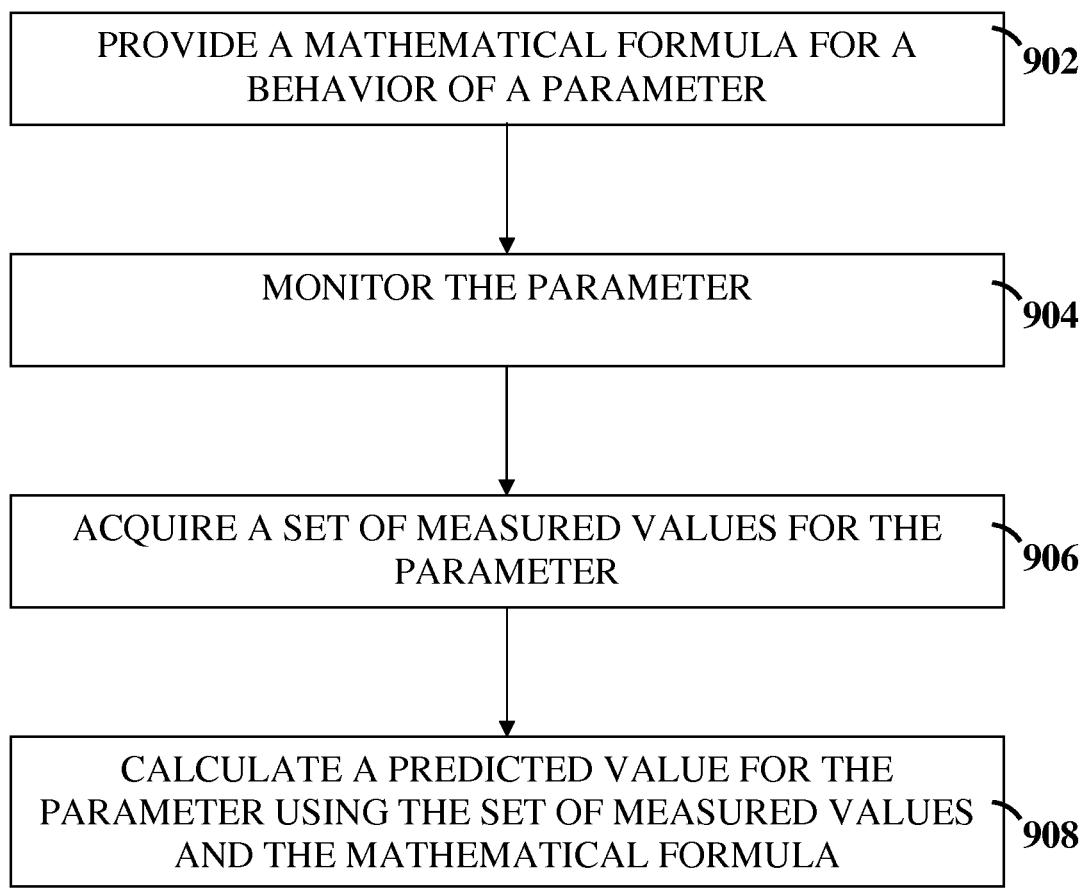
FIG. 9 illustrates a flowchart of a method used for predicting a terminal-value of a parameter.

Reference is now made to the flowchart of FIG. 9 representing the main steps in a method for predicting a terminal-value of a parameter.

The method commences with the step of providing a mathematical model 902 for the behavior of a parameter over time 902. For example, providing a mathematical model for expressing a relationship between a pressure reading as measured (typically in units of millimeters of mercury) by a single pressure-detection sensor in a sensing-mat over time.

It is noted that applying the method to a single sensor allows a predicted value to be obtained for each pressure sensor in a multi-sensor system. Applying the method to a plurality of sensors within a multi-sensor system may enable rapid measurement to be obtained by a pressure sensing-mat.

The procedure continues with the steps of monitoring the parameter 904 and acquiring a set of measured values for the parameter 906. The set of measured values for the parameter may be used for example for determining a time constant τ for which a final reading measurement may be expected.

Best-fit measurement readings may be selected from the measured values for example by using the method of least squares.

In the sensing-mat example, the time constant $\tau$ for each sensor is generally regarded as having a constant value over the time period of any given set of recorded values. However, the value of the time constant $\tau$ may change over longer time periods as a result of changes to the physical attributes of the sensing system. Variations in the time constant $\tau$ may be caused, for example, by changes in the elasticity of the insulation material over time. The estimated value of the time constant $\tau$ may be updated according to selected measurement readings of the sensors. Alternatively the time constant $\tau$ for a single sensor may be determined and updated according to time constant $\tau$ values of neighboring sensors.

The procedure continues with the calculation of a predicted value for the parameter based upon the set of measured values and the mathematical formula provided in the first step 908.

Upon initialization, the measured set of values may comprise a single measurement. That single measurement may be regarded as an initial baseline for determining the parameter value without applying predictive methods. Predictive methods may be applied only after a pre-defined set of values has been measured. The accuracy of value prediction is expected to increase as more values are acquired.

Some measured readings may be declared redundant if they are deemed to lie outside accepted normal ranges according to a variety of criteria such as obsolescence. These values are not typically used in the calculation of the predicted value although they may be recorded for further reference or disregarded altogether as suit requirements.

Figure 10:
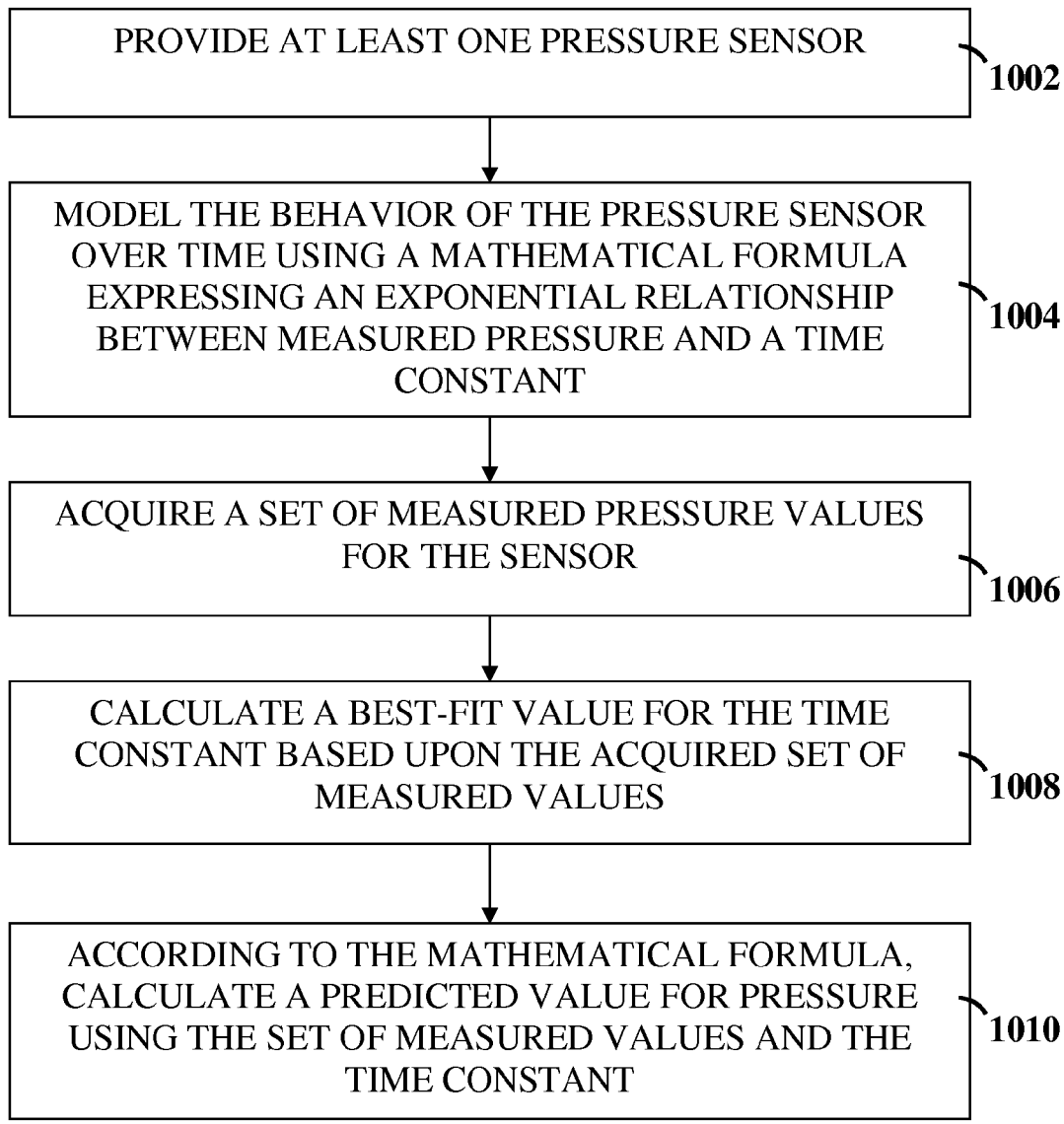
FIG. 10 illustrates a specific embodiment of a prediction method related to measuring pressure acting upon a surface.

Referring now to the flowchart of FIG. 10, the steps are shown of a particular embodiment of the method relating to measuring pressure acting upon a surface. At least one pressure-sensor is provided 1002, and the behavior of the pressure sensor is modeled by a mathematical formula expressing an exponential relationship between the measured pressure and a time-constant 1004. The method continues with the collection of a set of pressure readings over a time period 1006, and the calculation of a best-fit value for the time-constant based upon the set of the acquired pressure-values 1008. The procedure ends by using the best-fit value for the time-constant in the formula to calculate a predicted terminal-value for pressure 1010.

It should be noted that the method of FIG. 10 may be applied to a plurality of sensors within a pressure-detection sensing-mat. The method may be variously applied to individual pressure sensors, to selected sets of sensors of the sensing-mat, or to all the sensors comprising the sensing mat.

The sensors within the pressure-detection sensing mat may be organized as an array. The array may be multi-dimensional. The method may be applied to each of the individual sensors within the array or may be adjusted according to the values collected by neighboring sensors within the array.

Figure 11:
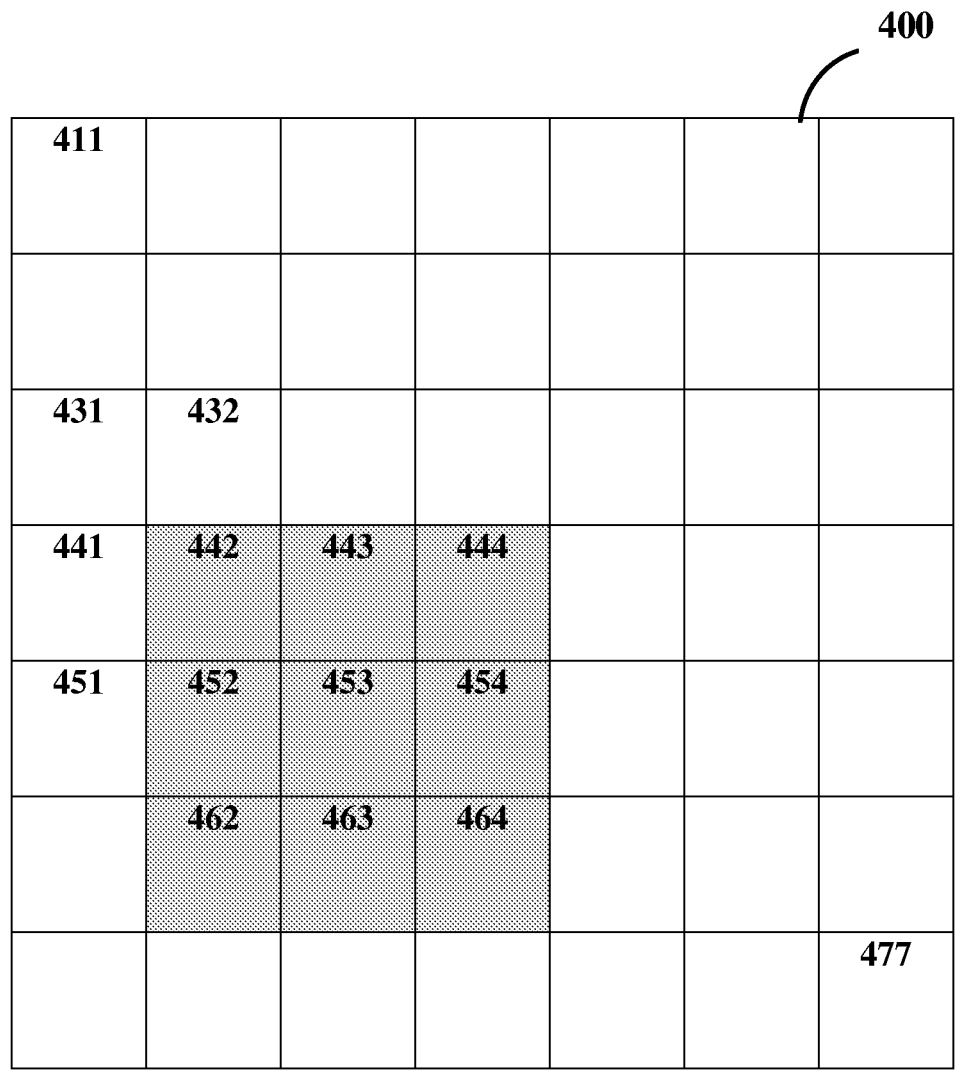
FIG. 11 is a schematic representation of a matrix of sensors.

Reference is now made to FIG. 11 showing a schematic representation of a seven-by-seven square array of sensors 400. The sensors are represented by squares arranged in a bi-directional array. Each sensor is indexed according to row and column, such that a sensor in row X and column Y is indexed 4XY. It will be appreciated that each sensor are surrounded by up to eight direct neighbors. For example, sensor 453 is surrounded by eight direct neighbors 442, 443, 444, 452, 454, 462, 463 and 464.

A set of pressure-values may be acquired over a time period by selecting a set of neighboring pressure-sensors from the array, and acquiring at least one pressure-reading measured by each member of the selected set of neighboring pressure sensors. The mathematical formula used to model the behavior of a parameter may be constructed using pressure values obtained from the whole set of neighboring sensors.

The mathematical formulae provided for two separate sensors within an array may differ. For example and without limitation, the formula for sensor 441 having only five neighboring sensors 431, 432, 442, 452, and 451 may be different from the formula provided for sensor 453 having eight neighbors as indicated above. Moreover, the selection of the set of neighboring sensors may be adapted to suit requirements, for example by including sensors that are not direct neighbors of a selected sensor.

Alternatively determining the estimated time constant $\tau$ for a single sensor such as 453 may be determined and updated according to estimated time constant $\tau$ values of its neighboring sensors. In such cases, the step of calculating a best-fit value for the time-constant $\tau$ based upon the acquired set of pressure-values may be further divided into the sub-steps of calculating a best-fit value for the time-constant for at least a selection of pressure-sensors from the set of neighboring pressure-sensors, and taking a mean value of the time-constant $\tau$ calculated for the selection of pressure-sensors.

Gain Selection

For illustrative purposes only, embodiments of a method for rapid high resolution measurement of a wide range of analog signals will be demonstrated through the particular example of a sensing mat comprising a plurality of pressure-detection sensors which may be arranged in a matrix such as described hereinabove. It will be appreciated however that the gain selection method described below may be usefully applied to other applications where high resolution rapid data sampling is required.

The values of analog signals obtained from pressure sensors may lie within a large range. As the measurement of weak signals may require greater amplification than the measurement of stronger signals, selection of an amplifier's gain level is commonly adjusted to maximize the highest recorded amplitude signal without reaching saturation. This approach may be used to fix a common gain for all signal types, and is useful when the signal range is relatively narrow. When a wide signal range is detected, a fixed gain level may result in either strong signal saturation or weak signal misinterpretation, thus preventing effective signal resolution and reducing the resolution of the sensor readings.

According to the sensing mat described hereinabove, each pressure-detection sensor monitors the capacitance between layers of conducting material. A layer of insulating material is sandwiched between two conductive material layers. Each sensor is configured such that pressing anywhere on its surface changes the spacing between the two conductive layers, and consequently the capacitance of the sensor.

It will be appreciated that the amplitude of AC current depends upon the impedance of the circuit. There is an inverse relationship between capacitance and impedance. As pressure is applied to the sensor the plates of the capacitor are pressed closer together increasing the capacitance. In response, the amplitude of the current tends to increase.

The sensing mat embodiment described hereinabove illustrates an example of a system in which a samples detected may have a wide range of values. It is noted that weak signals generally require amplification with a relatively high gain to obtain high resolution readings. However, the same high gain level may cause saturation of the stronger signals.

Figure 12:
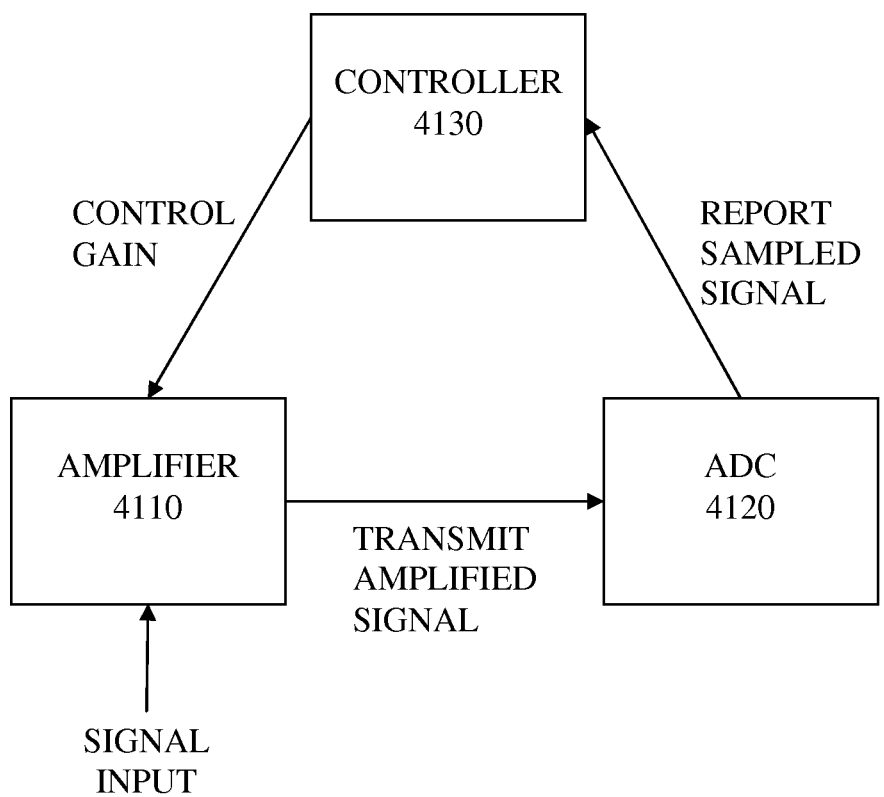
FIG. 12 is a block diagram representing the components used for a quick measurement method of a wide range of analog signals.

Reference is hereby made to the block diagram of FIG. 12, illustrating the main components of a system used for implementing a method for quick measurement of a wide range of analog signals at high resolution. The components include an amplifier 4110, an Analog to Digital Converter (ADC) 4120, and a controller 4130.

The amplifier 4110 is configured to receive analog signals from sensors as input. When a signal is received, the amplifier may be configured to amplify the signal by an initial gain level determined by the controller 4130. The signal amplified by the initial gain level may be transmitted to the Analog to Digital Converter (ADC) 4120. The ADC may be configured to sample the amplified signal, and to communicate the measurement to the control unit 4130. It is noted that where appropriate, multiple signals from a plurality of sensors may be amplified by a common amplifier.

In one embodiment, the amplifier is a variable gain amplifier which may be controlled by the control unit 4130. The gain level used for amplifying signals obtained from each sensor may be changed over time. The initial gain may be selected to be at any level, for example the midway gain level or half of the maximal gain level of the amplifier. Alternatively, the initial gain can be determined according to a first analog signal reading, or any other means.

In one embodiment, analog signals received from a particular sensor may be sampled by the ADC 4120 to determine their peak-to-peak range, by performing a binary search of the like.

It noted that a high speed Analog to digital converter (ADC) may be used to enable AC signal samples to be obtained at a variety of frequencies. For example, the AC signal can run at a rate of 100 kilohertz, and the current signal samples may be obtained at a rate of 3 Megahertz, such that 30 current samples may be obtained within one AC cycle. The minimum and maximum current readings may thereby be identified and declared as the peak values for the signal.

The controller 4130 may then determine the optimal peak-to-peak range for the signal from the sensor, as described hereinabove, and the optimal gain for the amplifier may be selected accordingly. In one embodiment, the optimal gain enables a signal amplitude which covers at least half of the optimal peak-to-peak range.

It should be appreciated that in the sensing mat embodiment, analog signal readings from each sensor are relatively stable over extended periods, and changes to the gain are not required very often. Factors which may require an update to the gain level used with each sensor include pressure changes and other factors affecting the capacitance of the sensors. In addition it will be appreciated that the gain level may need to be adjusted over time due to wear and tear of the mat.

The calculated optimal gain per sensor may be recorded, such that the controller may determine the gain to be used for measuring analog signals according to the previous gain values used for the same sensor.

Figure 13:
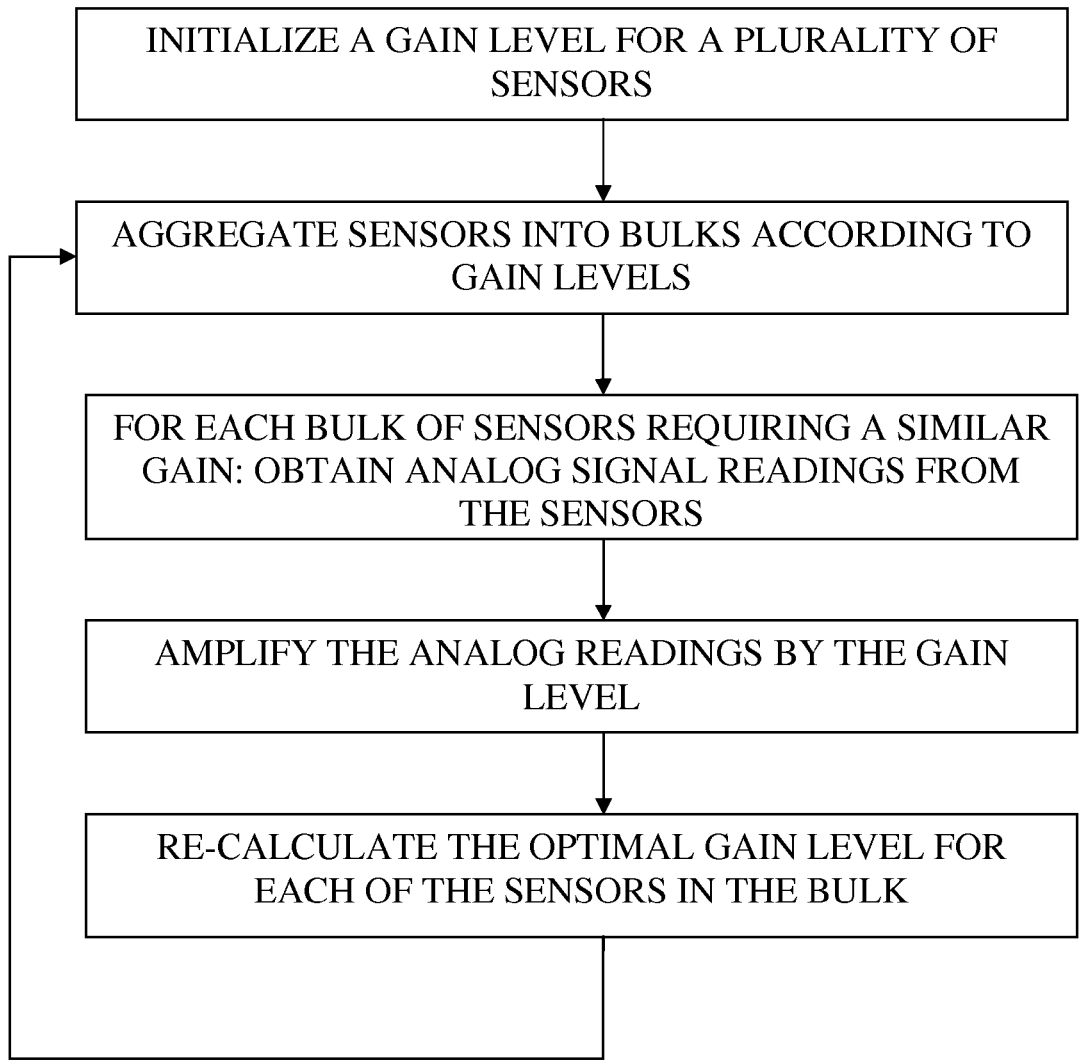
FIG. 13 is a flow chart illustrating the method for quick measurement of a wide range of analog signals.

This process may be duplicated for each of the pressure-detection sensors in the sensing mat. Furthermore, in order to facilitate efficient and rapid analog readings from a plurality of sensors, sensors may be aggregated in bulks according to their optimal gain. The amplifier may be configured with one gain value to amplify analog readings from the bulk of sensors suited for that gain value. The amplifier can later be configured with a second gain value to amplify analog sensor readings requiring the second gain. This process may then be repeated until all the signals from all the sensors are amplified, and is illustrated in FIG. 13.

The scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

The invention claimed is:

1. A method of measuring capacitances of n capacitors in a pressure sensing system including the pressure sensing system comprising: a plurality of linear conductor columns and a plurality of linear conductor rows, wherein the columns are not parallel to the rows, and an array of n capacitors each formed at an overlying region of a column and a row, and wherein the columns and rows are respectively disposed on opposite sides of a sheet of a compressible dielectric, the method comprising:
   applying an alternating known voltage to n circuits, each of the n circuits comprising a different bank of n−1 capacitors interconnected in parallel and the one remaining capacitor connected in series with the bank;
   measuring the alternating current of each of the n circuits;
   applying an alternating known voltage to an n+1 circuit comprising the n capacitors interconnected in parallel;
   measuring the alternating current of the n+1 circuit; and
   deriving from the measured current of each of the n circuits and the n+1 circuit and the known voltages of each of the n circuits and the n+1 circuits the capacitance of each of the n capacitors.

2. The method of claim 1 wherein the step of applying an alternating known voltage to n circuits comprises:
   applying an alternating known voltage between one row and a plurality of columns.

3. The method of claim 2 wherein the step of measuring the alternating current of each of the n circuits comprises:
   connecting a current sensor to one of the plurality of columns; and
   repeating the connecting for all of the plurality of columns.

4. The method of claim 2 wherein the plurality of columns comprises all the linear conductor columns of the pressure sensing system.

5. The method of claim 1 further comprising deriving a total capacitance of each n circuit from the known voltage of each of the n circuits and the measured current of each of the n circuits.

6. The method of claim 1 further comprising deriving a total capacitance of the n+1 circuit from the known voltage of the n+1 circuit and the measured current of the n+1 circuit.

7. A pressure sensing system comprising:
a sensing apparatus comprising an array of n capacitors each formed at an overlying region of a plurality of linear conductor columns and a plurality of linear conductor rows, and wherein the columns and rows are respectively disposed on opposite sides of a sheet of a compressible dielectric; and
a controller configured to:
apply an alternating known voltage to n circuits, each of the n circuits comprising a different bank of n−1 capacitors connected in parallel and the one remaining capacitor connected in series with the bank;
measure the alternating current of each of the n circuits;
apply an alternating known voltage to an n+1 circuit comprising n capacitors interconnected in parallel;
measure the alternating current of the n+1 circuit;
derive a capacitance of each of the n capacitors based on the measured current of each of the n circuits and the n+1 circuit and the known voltages of each of the n circuits and the n+1 circuits; and
determine a pressure exerted upon the sensing apparatus based on the capacitance of each of the n capacitors.

8. The system of claim 7 further comprising at least one variable gain amplifier and at least one analog-to-digital converter.

9. The system of claim 8 wherein the variable gain amplifier is configured to amplify at least one analog signal with an associated gain level.

10. The system of claim 8 wherein the controller is further configured to:
receive digital output signals from the analog to digital converter; and
calculate a gain level for associated analog input signals.

11. The system of claim 7 wherein the controller is further configured to:
monitor an amplitude of the measured alternating current signal of at least one of the n and n+1 circuits by collecting a plurality of current signal outputs during a time period T of the measured alternating current signal;
obtain a signal profile for the duration of the time period T;
identify a maximum-peak current signal output;
identify a minimum-peak current signal output; and
calculate the current difference between the maximum peak current signal output and the minimum peak current signal output.

12. The system of claim 7 wherein the controller is further configured to:
determine a terminal value for a parameter being monitored by the controller by providing a mathematical model for the behavior of the parameter over time, the model comprising a formula expressing a relationship between the parameter and at least one variable;
monitor the parameter;
acquire a plurality of measured values for the parameter over time;
calculate a best-fit set of values for the at least one variable based upon the plurality of measured values for the parameter; and
use the best-fit set of values and the formula to determine a predicted terminal-value of the parameter.

13. The system of claim 7 wherein the controller is further configured to:
derive a total capacitance of each n circuit from the known voltage of each of the n circuits and the measured current of each of the n circuits.

14. The system of claim 7 wherein the controller is further configured to:
derive a total capacitance of the n+1 circuit from the known voltage of the n+1 circuit and the measured current of the n+1 circuit.

15. A non-transitory computer-readable medium for measuring capacitances of a sensing apparatus and for determining the pressure exerted upon the sensing apparatus, the non-transitory computer-readable medium having computer-readable instructions stored thereon that are configured to execute the following functions:
apply an alternating known voltage to n circuits, each of the n circuits comprising a different bank of n−1 capacitors interconnected in parallel and one remaining capacitor connected in series with the bank;
measure the alternating current of each of the n circuits;
apply an alternating known voltage to an n+1 circuit comprising the n capacitors interconnected in parallel;
measure the alternating current of the n+1 circuit;
derive from the measured current of each of the n circuits and the n+1 circuit and the known voltages of each of the n circuits and the n+1 circuits the capacitance of each of the n capacitors; and
determine a pressure exerted upon the sensing apparatus based on the capacitance of each of the n capacitors.

16. The non-transitory computer-readable medium of claim 15, wherein the computer-readable instructions stored thereon are configured to execute the following further function:
apply an alternating known voltage between one row and a plurality of columns.

17. The non-transitory computer-readable medium of claim 15, wherein the computer-readable instructions stored thereon are configured to execute the following further functions:
connect a current sensor to one of the plurality of columns; and
repeat the connecting for all of the plurality of columns.

18. The non-transitory computer-readable medium of claim 15, wherein the computer-readable instructions stored thereon are configured to execute the following further functions:
derive a total capacitance of each n circuit from the known voltage of each of the n circuits and the measured current of each of the n circuits.

19. The non-transitory computer-readable medium of claim 15, wherein the computer-readable instructions stored thereon are configured to execute the following further functions:
derive a total capacitance of the n+1 circuit from the known voltage of the n+1 circuit and the measured current of the n+1 circuit.

20. The non-transitory computer-readable medium of claim 15, wherein the computer-readable instructions stored thereon are configured to execute the following further functions:
derive a total capacitance of each n circuit from the known voltage of each of the n circuits and the measured current of each of the n circuits; and
derive a total capacitance of the n+1 circuit from the known voltage of the n+1 circuit and the measured current of the n+1 circuit.

* * * * *